(12) United States Patent
Baker

(10) Patent No.: US 6,228,590 B1
(45) Date of Patent: May 8, 2001

(54) METHOD OF SELECTION FOR GENES ENCODING SECRETED AND TRANSMEMBRANE PROTEINS

(75) Inventor: Kevin P. Baker, Rockville, MD (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/273,163

(22) Filed: Mar. 19, 1999

Related U.S. Application Data

(60) Provisional application No. 60/079,010, filed on Mar. 23, 1998.

(51) Int. Cl.$^7$ .................................................. C12Q 1/68
(52) U.S. Cl. .................. 435/6; 435/254.11; 435/254.21
(58) Field of Search ........................ 435/6, 254.11, 435/254.21

(56) References Cited

U.S. PATENT DOCUMENTS

| | | | |
|---|---|---|---|
| 4,914,025 | 4/1990 | Manoil et al. | 435/69.8 |
| 5,037,760 | 8/1991 | Smith et al. | 435/320.1 |
| 5,041,376 | 8/1991 | Gething et al. | 435/6 |
| 5,182,195 | 1/1993 | Nakahama et al. | 435/69.1 |
| 5,212,070 | 5/1993 | Smith et al. | 435/69.1 |
| 5,498,832 | 3/1996 | Gausing et al. | 435/69.1 |
| 5,525,486 | 6/1996 | Honjo et al. | 435/69.1 |
| 5,536,636 | 7/1996 | Freeman, Jr. et al. | 435/6 |
| 5,536,637 | 7/1996 | Jacobs | 435/6 |
| 5,604,202 | 2/1997 | Kessler et al. | 514/12 |
| 5,709,859 | 1/1998 | Aruffo et al. | 424/134.1 |
| 5,712,116 | 1/1998 | Jacobs | 435/69.1 |

FOREIGN PATENT DOCUMENTS

| | | |
|---|---|---|
| 244042 | 11/1987 | (EP) . |
| 307247 | 3/1989 | (EP) . |
| 607054 | 7/1994 | (EP) . |
| 731169 | 9/1996 | (EP) . |
| WO 96/40904 | 12/1996 | (WO) . |
| WO 96/41609 | 12/1996 | (WO) . |

OTHER PUBLICATIONS

Green et al. The Jornal of Cell Biology. vol. 116(3): 597–604, Feb. 1992.*

Alam et al., "Reporter Genes: Application to the Study of Mammalian Gene Transcription" *Analytical Biochemistry* 188:245–254 (1990).

Biely et al., "A New Chromogenic Substrate for Assay and Detection of α–Amylase" *Analytical Biochemistry* 172:176–179 (1988).

Boeke et al., "A positive selection for mutants lacking orotidine–5'–phosphate decarboxylase activity in yeast: 5–fluoro–orotic acid resistance" *Molecular and General Genetics* 197:345–346 (1984).

Brodsky et al., "BiP and Sec63p are required for both co– and posttranslational protein translocation into the yeast endoplasmic reticulum" *Proc. Natl. Acad. Sci. USA* 92(21):9643–9646 (Oct. 10, 1995).

Brodsky, J.L., "Post–translational protein translocation: not all hsc70s are created equal" *Trends in Biochemical Sciences* 21(4):122–126 (Apr. 1996).

Bui et al., "Cloning and Expression of an Arxula Adeninivorans Glucoamylase Gene in *Saccharomyces Cerevisiae*" *Appl. Microbiol. Biotechnol.* 44:610–619 (1996).

Clarke et al., "A Colony Bank Containing Synthetic Col E1 Hybrid Plasmids Representative of the Entire *E. coli* Genome" *Cell* 9:91–99 (Sep. 1976).

Clementi et al., "α–Amylase and Glucoamylase Production by *Schwanniomyces Castellii*" *Antonie van Leeuwenhoek* 52:343–352 (1986).

Esnault et al., "The yeast SSS1 gene is essential for secretory protein translocation and encodes a conserved protein of the endoplasmic reticulum" *EMBO Journal* 12(11):4083–4093 (Nov. 1993).

Feldheim and Scheckman, "Sec72p contributes to the selective recognition of signal peptides by the secretory polypeptide translocation complex" *Journal of Cell Biology* 126(4):935–943 (Aug. 1994).

Feldheim et al., "Topology and Functional Domains of Sec63p, an Endoplasmic Reticulum Membrane Protein Required for Secretory Protein Translocation" *Molecular & Cellular Biology* 12(7):3288–3296 (Jul. 1992).

Felgner et al., "Lipofection: A Highly Efficient, Lipid–Mediated DNA–Transfection Procedure" *Proc. Natl. Acad. Sci. USA* 84:7413–7417 (Nov. 1987).

Finke et al., "A second trimeric complex containing homologs of the Sec61p complex functions in protein transport across the ER membrane of *S.cerevisiae*" *EMBO Journal* 15(7):1482–1494 (Apr. 1, 1996).

Gietz et al., "Improved Method for High Efficiency Transformation of Intact Yeast Cells" *Nucleic Acids Research* 20(6):1425 (1992).

Gilmore, R., "The protein translocation apparatus of the rough endoplasmic reticulum, its associated proteins, and the mechanism of translocation" *Current Opinion in Cell Biology* 3(4):580–584 (Aug. 1991).

Gubler et al., "A Simple and Very Efficient Method for Generating cDNA Libraries" *Gene* 25:263–269 (1983).

(List continued on next page.)

Primary Examiner—Remy Yucel
(74) Attorney, Agent, or Firm—Atulya R. Agarwal; Craig G. Svoboda; Mark T. Kresnak

(57) ABSTRACT

The present invention relates to a novel, improved method of identifying cDNA's which encode secreted and membrane-bound proteins. The methods of the invention provide for an improved signal sequence detection system using host strains deficient in post-translation translocation of siren sequences, which results in a greater number of correctly identified signal sequences and less total time required to complete the procedure.

29 Claims, 9 Drawing Sheets

OTHER PUBLICATIONS

Hanein et al., "Oligomeric Rings of the Sec61p Complex Induced by Ligands Required for Protein Translocation" *Cell* 87:721–732 (Nov. 15, 1996).

Hsu et al., "Coexpression of Molecular Chaperone BiP Improves Immunoglobulin Solubility and IgG Secretion from Trichoplusia ni Insect Cells" *Biotechnol. Prog.* 13(1):96–104 (1997).

Jacobs et al., "A Novel Method for Isolating Eukaryotic cDNA Clones Encoding Secreted Proteins" *Journal of Cellular Biochemistry* (Abstract No. C1–207) Suppl. 21A:19 (Mar. 1995).

Jensen et al., "Bacillus Acidopullulyticus Pullulanase: Application and Regulatory Aspects for Use in the Food Industry" *Process Biochemistry* 19:129–134 (Aug. 1984).

Kaiser et al., "Many Random Sequences Functionally Replace the Secretion Signal Sequence of Yeast Invertase" *Science* 235:312–317 (Jan. 16, 1987).

Kaiser et al., "Media" *Methods in Yeast Genetics* (Appendix A), 1994 edition, Cold Spring Harbor, N.Y.:Cold Spring Harbor Laboratory Press pp. 207–210 (1994).

Kaiser et al., "Protein Secretion, Membrane Biogenesis, and Endocytosis" *Molecular and Cellular Biology of the Yeast Saccharomyces: Cell Cycle and Cell Biology,* Pringle,J.R, Broach,J.R. and Jones,E.W., eds., Cold Spring Harbor Laboratory Press, Chapter 2, pp. 91–227 (1997).

Kaiser et al., "Secretion–Defective Mutations in the Signal Sequence for *Saccharomyces cerevisiae* Invertase" *Molecular & Cellular Biology* 6(7):2382–2391 (Jul. 1986).

Kato et al., "Construction of a Human Full–Length cDNA Bank" *Gene* 150:243–250 (1994).

Kawamura–Watabe et al., "Isolation and Characterization of kar2–404 Mutation in *Saccharomyces cerevisiae*" *Biosci. Biotech. Biochem.* 61(7):1172–1178 (Jul. 1997).

Kean et al., "Retrograde Lipid Traffic in Yeast: Identification of Two Distinct Pathways for Internalization and Fluorescent–labeled Phosphatidylcholine from the Plasma Membrane" *Journal of Cell Biology* 123(6, pt 1):1403–1419 (Dec. 1993).

Kjeldsen et al., "Synthetic Leaders with Potential BiP Binding Mediate High–Yield Secretion of Correctly Folded Insulin Precursors from *Saccharomyces cerevisiae*" *Protein Expression and Purification* 9(3):331–336 (Apr. 1997).

Kuehn et al., "COPII–cargo interactions direct protein sorting into ER–derived transport vesicles" *Nature* 391(6663):187–190 (Jan. 8, 1998).

Lopata et al., "High Level Transient Expression of a Chloramphenicol Acetyl Transferase Gene by DEAE–Dextran Mediated DNA Transfection Coupled with a Dimethyl Sulfoxide or Glycerol Shock Treatment" *Nucleic Acids Research* 12(14):5707–5717 (1984).

Lyman et al., "Binding of Secretory Precursor Polypeptides to a Translocon Subcomplex is Regulated by BiP" *Cell* 88(1):85–96 (Jan. 10, 1997).

Lyman et al., "Polypeptide translocation machinery of the yeast endoplasmic reticulum" *Experientia* 52(12):1042–1049 (Dec. 15, 1996).

Mandel et al., "Calcium–dependent Bacteriophage DNA Infection" *Journal of Molecular Biology* (Letter to the Editor) 53:159–162 (1970).

Manners, D., "Recent Developments in Our Understanding of Amylopectin Structure" *Carbohydr. Pol.* 11:87–112 (1989).

McCann et al., "The Utilization of Starch by Yeasts" *Yeast* 2:109–115 (1986).

Messing et al., "Filamentous Coliphage M13 as a Cloning Vehicle: Insertion of a HindII Fragment of the lac Regulatory Region in M13 Replicative Form in vitro" *Proc. Natl. Acad. Sci. USA* 74(9):3642–3646 (Sep. 1977).

Messing, J., "New M13 Vectors for Cloning" *Methods in Enzymology,* Academic Press vol. 101:20–78 (1983).

Miller et al., "High–Voltage Electroporation of Bacteria: Genetic Transformation of Campylobacter Jejuni with plasmid DNA" *Proc. Natl. Acad. Sci. USA* 85:856–860 (Feb. 1988).

Mizuta et al., "Continued Functioning of the Secretory Pathway is Essential for Ribosome Synthesis" *Molecular & Cellular Biology* 14(4):2493–2502 (Apr. 1994).

Modena et al., "Biochemical and Immunological Characterization of the STA2–Encoded Extracellular Glucoamylase from *Saccharomyces Diastaticus*" *Archives of Biochemistry & Biophysics* 248(1):138–150 (Jul. 1986).

Morris et al., "Immunoglobulin Binding Protein (BiP) Function Is Required to Protect Cells from Endoplasmic Reticulum Stress but Is Not Required for the Secretion of Selective Proteins" *Journal of Biological Chemistry* 272(7):4327–4334 (Feb. 14, 1997).

Nakamura et al., "Sequences of cDNAs for Human Salivary and Pancreatic α–Amylase" *Gene* 28:263–270 (1984).

Ng et al., "Signal Sequences Specify the Targeting Route to the Endoplasmic Reticulum Membrane" *Journal of Cell Biology* 134(2):269–278 (Jul. 1996).

Nishide et al., "Corrected Sequences of cDNAs for Human Salivary and Pancreatic α–Amylase" *Gene* 50:371–372 (1986).

Ohtsuka, K., "Cloning of a cDNA for Heat–Shock Protein hsp40, A Human Homologue of Bacterial DnaJ" *Biochemical & Biophysical Research Communications* 197(1):235–240 (Nov. 30, 1993).

Okayama et al., "High–Efficiency Cloning of Full–Length cDNA" *Molecular & Cellular Biology* 2(2):161–170 (Feb. 1982).

Post–Beittenmiller et al., "Regulation of Basal and Induced Levels of the MEL1 Transcript in *Saccharomyces cerevisiae*" *Molecular & Cellular Biology* 4(7):1238–1245 (Jul. 1984).

Rothstein, R., "Targeting, Disruption, Replacement, and Allele Rescue: Integrative DNA Transformation in Yeast" *Methods in Enzymology,* Guthrie, C. and Fink, G.R., eds., San Diego:Academic Press, Chapter 19, vol. 194:281–301 (1991).

Schekman, R., "Polypeptide Translocation: A Pretty Picture Is Worth a Thousand Words" *Cell* 87:593–595 (Nov. 15, 1996).

Scidmore et al., "Genetic Interactions Between KAR2 and SEC63, Encoding Eukaryotic Homologues of DnaK and DnaJ in the Endoplasmic Reticulum" *Molecular Biology of the Cell* 4(11):1145–1159 (Nov. 1993).

Seed et al., "Representation of DNA Sequences in Recombinant DNA Libraries Prepared by Restriction Enzyme Partial Digestion" *Gene* 19:201–209 (1982).

Shibuya et al., "Cloning of the α–Amylase cDNA of *Aspergillus Shirousamii* and Its Expression in *Saccharomyces Cerevisiae*" *Biosci. Biotech. Biochem.* 56(2):174–179 (1992).

Shibuya et al., "Molecular Cloning of the Glucoamylase Gene of *Aspergillus Shirousami* and Its Expression in *Aspergillus Oryzae*" *Agric. Biol. Chem.* 54(8):1905–1914 (1990).

Shigekawa et al., "Electroporation of Eukaryotes and Prokaryotes: A General Approach to the Introduction of Macromolecules into Cells" *BioTechniques* 6(8):742–751 (1988).

Silve et al., "In vivo translocation of the cell wall acid phosphates across the yeast endoplasmic reticulum membrane: are there multiple signals for the targeting process?" *Biochimie* 72:103–114 (1990).

Soloman, B., "Starch Hydrolysis by Immobilized Enzymes Industrial Applications" *Advances in Biochemical Engineering,* New York:Springer Berlin Heidelberg vol. 10:131–177 (1978).

Vahlensieck et al., "Transcriptional Studies on Yeast SEC Genes Provide no Evidence for Regulation at the Transcriptional Level" *Yeast* 11(10):901–911 (Aug. 1995).

Vieira et al., "Production of Single–stranded Plasmid DNA" *Methods in Enzymology* 153:3–11 (1987).

von Heijne, G., "Signal Sequences: The Limits of Variation" *Journal of Molecular Biology* 184:99–105 (1985).

von Heijne, G., "The Signal Peptide" *Journal of Membrane Biology* 115:195–201 (1990).

Wainwright et al., "Quality control of glycosylphosphatidylinositol anchor attachment in mammalian cells: a biochemical study" *Biochemical Journal* 321(pt 3):655–664 (Feb. 1, 1997).

Yanisch–Perron et al., "Improved M13 Phage Cloning Vectors and Host Strains: Nucleotide Sequences of the M13mp18 and pUC19 Vectors" *Gene* 33:103–119 (1985).

Zhang et al., "Quality Control in the Secretory Pathway: The Role of Calreticulin, Calnexin and BiP in the Retention of Glycoproteins with C–Terminal Truncations" *Molecular Biology of the Cell* 8(10):1943–1954 (Oct. 1997).

Fang et al., "Nonlethal sec71–1 and sec72–1 mutations eliminate proteins associated with the sec63p–BiP complex from *S. cerevisiae*" *Molecular Biology of the Cell* 5(9):933–942 (Sep. 1994).

Green et al., "Mutants in three novel complementation groups inhibit membrane protein insertion into and soluble protein translocation across the endoplasmic reticulum membrane of *Saccharomyces cerevisiae*" *Journal of Cell Biology* 116(3):597–604 (Feb. 1992).

Jacobs et al., "A genetic selection for isolating cDNAs encoding secreted proteins" *Gene* 198:289–296 (Oct. 1, 1997).

Klein et al., "Selection for Genes Encoding Secreted Proteins and Receptors" *Proc. Natl. Acad. Sci. USA* 93(14):7108–7113 (Jul. 9, 1996).

Kurihara et al., "Suppression of a sec63 Mutation Identifies a Novel Component of the Yeast Endoplasmic Reticulum Translocation Apparatus" *Molecular Biology of the Cell* 4(9):919–930 (Sep. 1993).

* cited by examiner

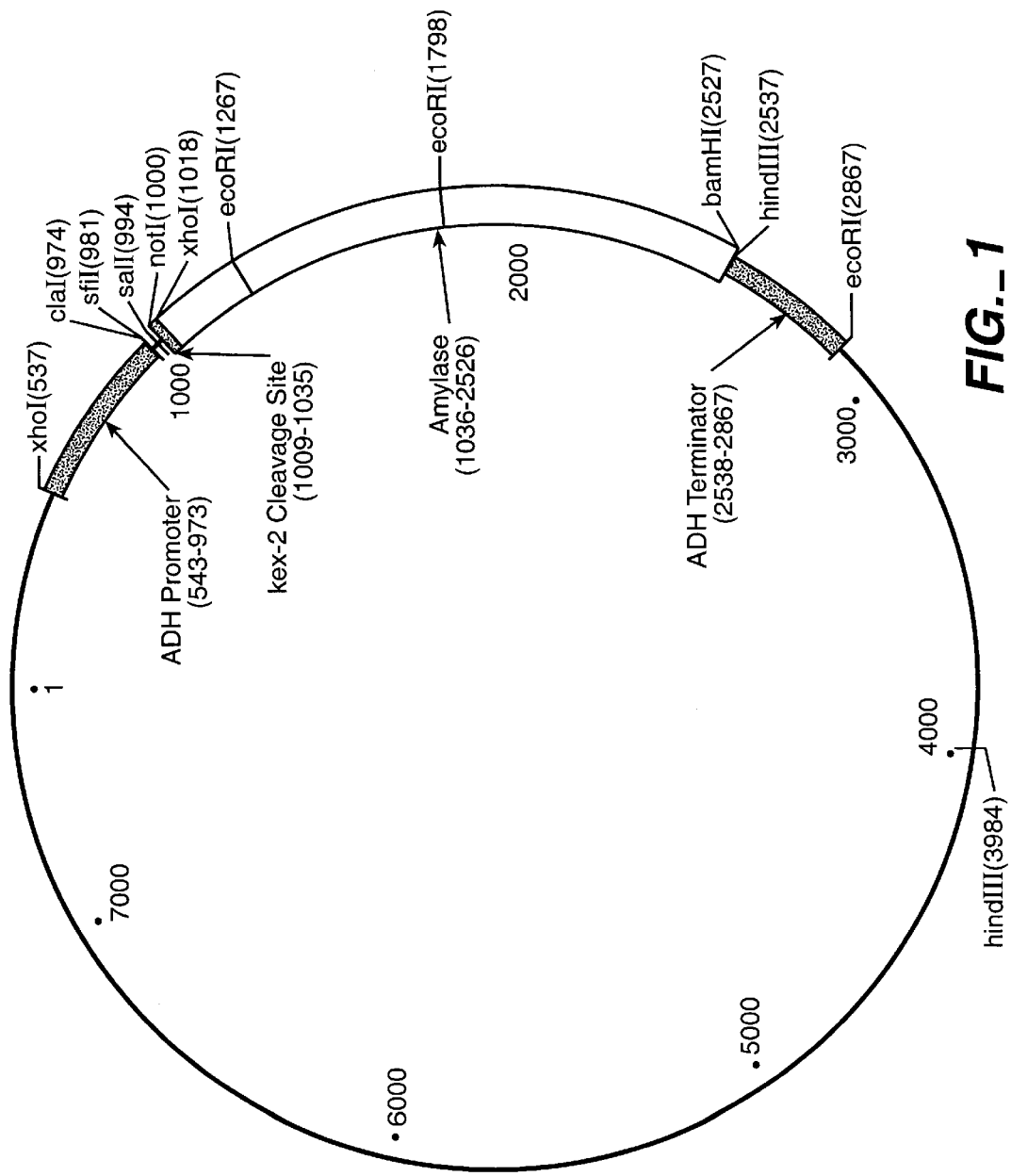
FIG._1

INVERTASE

1. TRANSFORMATION
   SELECT ON SCD-URA
   3 DAYS

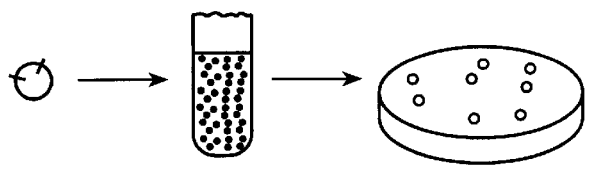

2. REPLICA PLATE
   ONTO YEP-SUCROSE
   7-10 DAYS

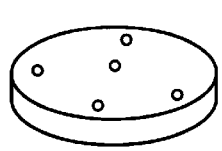

3. PICK POSITIVES
   RESTREAK ON YEP-SUCROSE
   5-7 DAYS

4. SINGLE COLONY PCR
   GEL ANALYSIS
   PURIFY DNA
   SEQUENCE

TOTAL TIME = 16-21 DAYS

AMYLASE

1. TRANSFORMATION
   SELECT ON SCD-URA / STARCH
   OR SCD-URA / RED STARCH
   3 DAYS

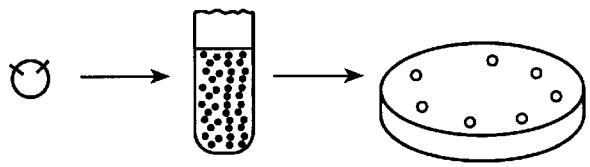

2. PICK POSITIVES: RESTREAK
   3 DAYS

3. SINGLE COLONY PCR
   GEL ANALYSIS
   PURIFY DNA
   SEQUENCE

TOTAL TIME = 6-7 DAYS

FIG._2

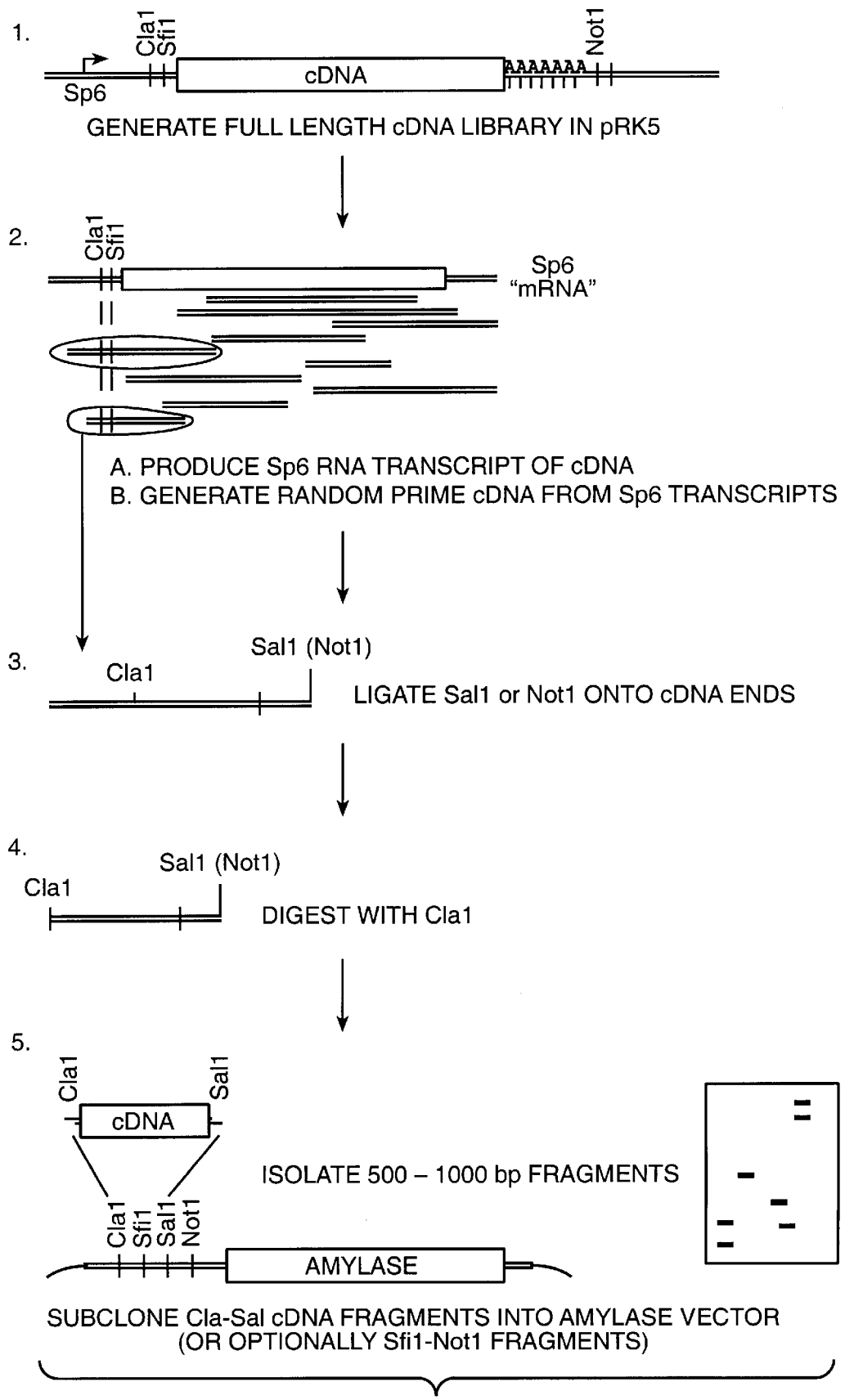
FIG._3

MAFKDTGKTPVEPEVAIHRIRITLTSRNVKSLEKVCADLIRGAKEKNLKVKGPVRMPTKT
LRITTRKTPCGEGSKTWDRFQMRIHKRLIDLHSPSEIVKQITSISIEPGASANHVAAANW
AAGVSLEKREAQYDPHTQYGRTAIIHLFEWRWVDIAKECERYLAPNGFAGVQVSPPNENI
VVHSPSRPWWERYQPISYKICSRSGNEDEFRDMVNRCNNVGVRIYVDAVINHMCGVGAQA
GQSSTCGSYFNPNNRDFPGVPYSGFDFNDGKCRTASGGIENYQDAAQVRDCRLSGLLDLA
LEKDYVRTKVADYMNHLIDIGVAGFRLDASKHMWPGDIKAILDKLHNLNTKWFSQGSRPF
IFQEVIDLGGEAVSSNEYFGNGRVTEFKYGAKLGKVMRKWDGEKMSYLKNWGEGWGLMPS
DRALVFVDNHDNQRGHGAGGASILTFWDARLYKMAVGFMLAHPYGFTRVMSSYYWPRNFQ
NGKDVNDWVGPPNNNGKTKEVSINPDSTCGNDWICEHRWRQIRNMVAFRNVVNGQPFANW
WDNDSNQVAFGRGNKGLIVFNNDDWALSETLQTGLPAGTYCDVISGDKVDGNCTGIKVYV
GNDGKAHFSISNSAEDPFIAIHAESKI (SEQ ID NO: 4)

FIG._4

MLCQIKKVKVQSRAAANWAAGVSLEKREAQYDPHTQYGRTAIIHLFEWRWVDIAKECERYLAPNG
FAGVQVSPPNENIVVHSPSRPWWERYQPISYKICSRSGNEDEFRDMVNRCNNVGVRIYVDAVINH
MCGVGAQAGQSSTCGSYFNPNNRDFPGVPYSGFDFNDGKCRTASGGIENYQDAAQVRDCRLSGLL
DLALEKDYVRTKVADYMNHLIDIGVAGFRLDASKHMWPGDIKAILDKLHNLNTKWFSQGSRPFIF
QEVIDLGGEAVSSNEYFGNGRVTEFKYGAKLGKVMRKWDGEKMSYLKNWGEGWGLMPSDRALVFV
DNHDNQRGHGAGGASILTFWDARLYKMAVGFMLAHPYGFTRVMSSYYWPRNFQNGKDVNDWVGPP
NNNGKTKEVSINPDSTCGNDWICEHRWRQIRNMVAFRNVVNGQPFANWWDNDSNQVAFGRGNKGL
IVFNNDDWALSETLQTGLPAGTYCDVISGDKVDGNCTGIKVYVGNDGKAHFSISNSAEDPFIAIH
AESKI (SEQ ID NO: 5)

FIG._6

MRALAVLSVTLVMACTEAFFPFISRGKNSFWGKAEESRVSSVLEESKRLVDTAMYATMQRNLKKR
GILSPAQLLSFSKLPEPTSGVIARXAEIMETSXQAMKRKVNLKTQQSQHPTDALSEDLLSIIANM
SGCLPYMLPPKCPNTCHVAAANWAAGVSLEKREAQYDPHTQYGRTAIIHLFEWRWVDIAKECERY
LAPNGFAGVQVSPPNENIVVHSPSRPWWERYQPISYKICSRSGNEDEFRDMVNRCNNVGVRIYVD
AVINHMCGVGAQAGQSSTCGSYFNPNNRDFPGVPYSGFDFNDGKCRTASGGIENYQDAAQVRDCR
LSGLLDLALEKDYVRTKVADYMNHLIDIGVAGFRLDASKHMWPGDIKAILDKLHNLNTKWFSQGS
RPFIFQEVIDLGGEAVSSNEYFGNGRVTEFKYGAKLGKVMRKWDGEKMSYLKNWGEGWGLMPSDR
ALVFVDNHDNQRGHGAGGASILTFWDARLYKMAVGFMLAHPYGFTRVMSSYYWPRNFQNGKDVND
WVGPPNNNGKTKEVSINPDSTCGNDWICEHRWRQIRNMVAFRNVVNGQPFANWWDNDSNQVAFGR
GNKGLIVFNNDDWALSETLQTGLPAGTYCDVISGDKVDGNCTGIKVYVGNDGKAHFSISNSAEDP
FIAIHAESKI (SEQ ID NO: 6)

FIG._8

MSEFNETKFSNNGTFFETEEPIVETKSISVYTPLIYVFILVVSLVMFASSYRKKQAKKIS
EQPSIFDENDAHDLYFQIKEMSENEKIHEKVLKAALLNRGAESVRRSLKLKELAPQINLL
YKNGSIGEDYWKRFETEVKLIELEFKDTLQEAERLQPGWVQLFVMVCKEICFNQALSRRY
QSILKRKEVCIKEWELKINNDGRLVN (SEQ ID NO: 7)

MSEFNETKFSNNGTFFETEEPIVETKSISVYTPLIYVFILVVSLVMFASSYRKKQAKKIS
EQPSIFDENDAHDLYFQIKEMSENEKIHEKVLKAALLNRGAESVRRSLKLKELAPQINLL
YK*KWLYWGGLLEEI* (SEQ ID NO: 8)

FIG._10

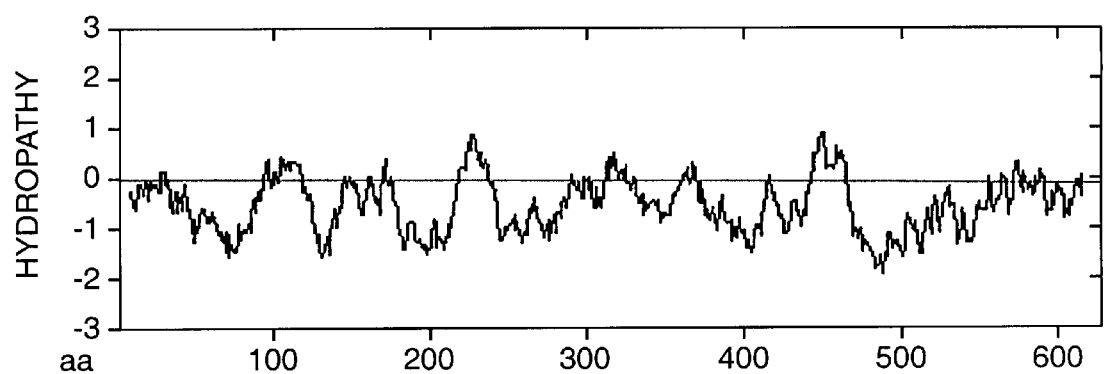
FIG._5
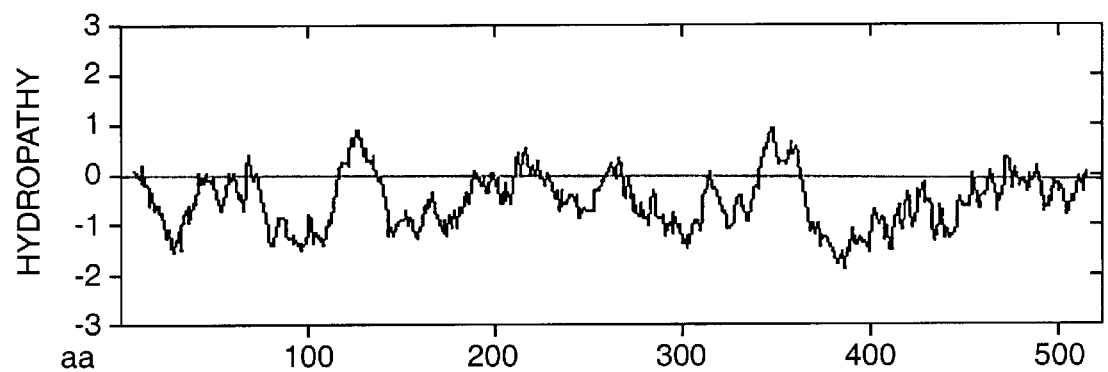
FIG._7
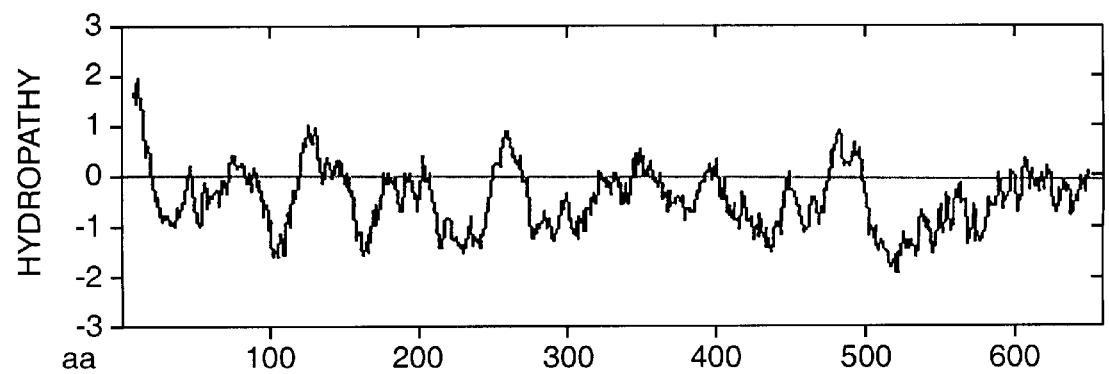
FIG._9

```
              10         20         30         40         50
phE3.full   GATTACGCCAAGCTTGCATGCCAGCATGTCACCGTGCTTTAGTCCTAGAT
            *************************************************
phB.full        ACGCCAAGCTTGCATGCCAGCATGTCACCGTGCTTTAGTCCTAGAT
                  10         20         30         40

60         70         80         90        100
phE3.full   CCATCACTGTTCGATCAGCTAGTTCAGAAACAGCATGAATACCTTGACCG
            *************************************************
phB.full    CCATCACTGTTCGATCAGCTAGTTCAGAAACAGCATGAATACCTTGACCG
              50         60         70         80         90

110        120        130        140        150
phE3.full   GGCTTCTCACAAACAGTAAATGTGTCGACATCGGCATTGGGGTCCAGATT
            *************************************************
phB.full    GGCTTCTCACAAACAGTAAATGTGTCGACATCGGCATTGGGGTCCAGATT
             100        110        120        130        140

160        170        180        190        200
phE3.full   ACCCACCAACTTTTCAATGACCGTTCCGAAAAGGTCGTTTTCTTGACAAG
            *************************************************
phB.full    ACCCACCAACTTTTCAATGACCGTTCCGAAAAGGTCGTTTTCTTGACAAG
             150        160        170        180        190

210        220        230        240        250
phE3.full   AAACCCTGTGTGTACCGTTTTTTGATCTAAATCTGATAAGCATACTTCAC
            *************************************************
phB.full    AAACCCTGTGTGTACCGTTTTTTGATCTAAATCTGATAAGCATACTTCAC
             200        210        220        230        240

260        270        280        290        300
phE3.full   TTAAATGTATATCGATATCAGTAGTATAGGGAAATTTTTCTTCAGAGTAC
            *************************************************
phB.full    TTAAATGTATATCGATATCAGTAGTATAGGGAAATTTTTCTTCAGAGTAC
             250        260        270        280        290

310        320        330        340        350
phE3.full   TGTCCTATTATTTGCCACTCTTCGTTCTGTATGTTACGAGGGCGTTCCTT
            *************************************************
phB.full    TGTCCTATTATTTGCCACTCTTCGTTCTGTATGTTACGAGGGCGTTCCTT
             300        310        320        330        340

360        370        380        390        400
phE3.full   AAAATGGGTAGACGCATCTTATTACCCGCCAAAAAACGTCAAAAGTTTTA
            *************************************************
phB.full    AAAATGGGTAGACGCATCTTATTACCCGCCAAAAAACGTCAAAAGTTTTA
             350        360        370        380        390
```

FIG._11A

```
                    410       420       430       440       450
phE3.full    GGAACACGTCTAAAAGTTGAAATAATATGTGAAAAAATTGATGAAATATT
             **************************************************
phB.full     GGAACACGTCTAAAAGTTGAAATAATATGTGAAAAAATTGATGAAATATT
                400       410       420       430       440

460       470       480       490       500
phE3.full    AATGAAATGGCTTATTTAAACGAATTCAAGTACAGGAAAGAGGTACGCAC
             **************************************************
phB.full     AATGAAATGGCTTATTTAAACGAATTCAAGTACAGGAAAGAGGTACGCAC
                450       460       470       480       490

510       520       530       540       550
phE3.full    AACTACTTGAGTTTGCCAATATGTCCGAATTTAATGAAACAAAATTCTCC
             **************************************************
phB.full     AACTACTTGAGTTTGCCAATATGTCCGAATTTAATGAAACAAAATTCTCC
                500       510       520       530       540

560       570       580       590       600
phE3.full    AACAACGGGACGTTTTTTGAAACGGAAGAGCCAATTGTGGAGACGAAATC
             **************************************************
phB.full     AACAACGGGACGTTTTTTGAAACGGAAGAGCCAATTGTGGAGACGAAATC
                550       560       570       580       590

610       620       630       640       650
phE3.full    AATCTCCGTTTATACCCCACTCATATATGTCTTTATTCTGGTGGTGTCCC
             **************************************************
phB.full     AATCTCCGTTTATACCCCACTCATATATGTCTTTATTCTGGTGGTGTCCC
                600       610       620       630       640

660       670       680       690       700
phE3.full    TTGTGATGTTTGCTTCAAGCTACAGAAAGAAGCAGGCCAAAAAAATTAGT
             **************************************************
phB.full     TTGTGATGTTTGCTTCAAGCTACAGAAAGAAGCAGGCCAAAAAAATTAGT
                650       660       670       680       690

710       720       730       740       750
phE3.full    GAGCAACCATCCATATTTGACGAAAACGATGCCCATGATCTGTATTTCCA
             **************************************************
phB.full     GAGCAACCATCCATATTTGACGAAAACGATGCCCATGATCTGTATTTCCA
                700       710       720       730       740

760       770       780       790       800
phE3.full    AATAAAGGAAATGAGTGAAATGAAAAAATTCACGAGAAGGTGTTGAAGG
             **************************************************
phB.full     AATAAAGGAAATGAGTGAAATGAAAAAATTCACGAGAAGGTGTTGAAGG
                750       760       770       780       790
```

FIG._11B

```
              810        820        830        840        850
phE3.full   CCGCTTTATTGAACAGAGGAGCAGAATCTGTTAGACGATCATTAAAGTTA
            **************************************************
phB.full    CCGCTTTATTGAACAGAGGAGCAGAATCTGTTAGACGATCATTAAAGTTA
              800        810        820        830        840

860        870        880        890        900
phE3.full   AAAGAGTTGGCTCCTCAGATAAACCTTCTATATAAAAAATGGCTCTATTG
            ******************************* ******************
phB.full    AAAGAGTTGGCTCCTCAGATAAACCTTCTATAT-AAAAATGGCTCTATTG
              850        860        870        880        890

910        920        930        940        950
phE3.full   GGGAGGATTACTGGAAGAGATTTGAAACTGAAGTTAAATTAATTGAATTG
            **************************************************
phB.full    GGGAGGATTACTGGAAGAGATTTGAAACTGAAGTTAAATTAATTGAATTG
              900        910        920        930        940

960        970        980        990       1000
phE3.full   GAATTTAAAGATACTTTACAAGAAGCTGAAAGATTGCAACCGGGCTGGGT
            **************************************************
phB.full    GAATTTAAAGATACTTTACAAGAAGCTGAAAGATTGCAACCGGGCTGGGT
              950        960        970        980        990

1010       1020       1030       1040       1050
phE3.full   TCAATTGTTCGTTATGGTTTGTAAAGAAATTTGCTTTAATCAAGCTCTCT
            **************************************************
phB.full    TCAATTGTTCGTTATGGTTTGTAAAGAAATTTGCTTTAATCAAGCTCTCT
             1000       1010       1020       1030       1040

1060       1070       1080       1090       1100
phE3.full   CTAGACGTTATCAATCAATCTTGAAACGGAAAGAAGTGTGTATTAAAGAG
            **************************************************
phB.full    CTAGACGTTATCAATCAATCTTGAAACGGAAAGAAGTGTGTATTAAAGAG
             1050       1060       1070       1080       1090

1110       1120       1130       1140       1150
phE3.full   TGGGAGCTGAAAATAAATAATGATGGAAGATTAGTCAATTAGTGCCTACT
            **************************************************
phB.full    TGGGAGCTGAAAATAAATAATGATGGAAGATTAGTCAATTAGTGCCTACT
             1100       1110       1120       1130       1140

1160       1170       1180       1190       1200
phE3.full   GTGTGCAAAGATATGTATTCGCTCGTTCAGTGTTTTTTTAAAAATATGTA
            **************************************************
phB.full    GTGTGCAAAGATATGTATTCGCTCGTTCAGTGTTTTTTTAAAAATATGTA
             1150       1160       1170       1180       1190
```

FIG._11C

```
              1210       1220       1230       1240       1250
phE3.full  TAGAATTTGTCATTATCTGCGTTAAAAAATAGTTATAAAGTATATACAAT
           **************************************************
phB.full   TAGAATTTGTCATTATCTGCGTTAAAAAATAGTTATAAAGTATATACAAT
              1200       1210       1220       1230       1240

1260       1270       1280       1290       1300
phE3.full  AACAATAAATGATAAAGAAATATGCAGTGAAAAGAAAAAATTATGAAGCT
           **************************************************
phB.full   AACAATAAATGATAAAGAAATATGCAGTGAAAAGAAAAAATTATGAAGCT
              1250       1260       1270       1280       1290

1310       1320       1330       1340       1350
phE3.full  TTTCCTTTCAGTGTTTTCTACCCTTCTTCTTGCTCACTACTTGGAATTCC
           **************************************************
phB.full   TTTCCTTTCAGTGTTTTCTACCCTTCTTCTTGCTCACTACTTGGAATTCC
              1300       1310       1320       1330       1340

1360       1370       1380       1390       1400
phE3.full  CAGCCGTCGTCATCATTGCCTGATAGAGCTAGCGCTTCATTCCAACTTAG
           **************************************************
phB.full   CAGCCGTCGTCATCATTGCCTGATAGAGCTAGCGCTTCATTCCAACTTAG
              1350       1360       1370       1380       1390

1410       1420       1430       1440       1450
phE3.full  TGGATCATCACCTTGTTTTTCGCACGCAACACGTCTTTTAATAAATTCAG
           **************************************************
phB.full   TGGATCATCACCTTGTTTTTCGCACGCAACACGTCTTTTAATAAATTCAG
              1400       1410       1420       1430       1440

1460       1470       1480       1490       1500
phE3.full  TGGCAAATCTTCTACCATCCATAACGTCACTATTGGCATAAATTGTTTCT
           **************************************************
phB.full   TGGCAAATCTTCTACCATCCATAACGTCACTATTGGCATAAATTGTTTCT
              1450       1460       1470       1480       1490

1510       1520       1530       1540       1550
phE3.full  TGAATCAATTCTTTAGATTCTGGCCCCGTAGGTAAACTCAATAATAGTTC
           **************************************************
phB.full   TGAATCAATTCTTTAGATTCTGGCCCCGTAGGTAAACTCAATAATAGTTC
              1500       1510       1520       1530       1540

1560       1570       1580       1590       1600
phE3.full  TAAGACATTGTTATTGGTTATTCCAGAATTTAATTTCATCTGTGATTTAC
           **************************************************
phB.full   TAAGACATTGTTATTGGTTATTCCAGAATTTAATTTCATCTGTGATTTAC
              1550       1560       1570       1580       1590

1610       1620       1630       1640       1650
phE3.full  ACCATTTGATAAATTCTTGCCGGGGAGAAACATTGTTCATGCTAGCAAAG
           **************************************************
phB.full   ACCATTTGATAAATTCTTGCCGGGGAGAAACATTGTTCATGCTAGCAAAG
              1600       1610       1620       1630       1640

1660       1670       1680
phE3.full  GTAGTGGTAGTAGAAGTCTCGACTCTAGAGGATCCCCGG(SEQ ID NO:10)
           ***************************************
phB.full   GTAGTGGTAGTAGAAGTCTCGACTCTAGAGGATCCCCGG(SEQ ID NO: 9)
              1650       1660       1670       1680
```

FIG._11D

METHOD OF SELECTION FOR GENES ENCODING SECRETED AND TRANSMEMBRANE PROTEINS

This is a non-provisional application of co-pending application provisional application No. 60/079,010 filed Mar. 23, 1998, the entire disclosure of which is hereby incorporated by reference and to which application priority is claimed under 35 USC §119.

TECHNICAL FIELD

The present invention relates to a novel method of identifying nucleic acid sequences encoding secreted and membrane-bound proteins based upon the presence of signal sequences.

BACKGROUND

Extracellular proteins are essential in the formation, differentiation and maintenance of multicellular organisms. The determination by individual cells of whether to live, proliferate, migrate, differentiate, interact with other cells or secrete are governed by information received from the cells neighbors and the immediate environment. This information is often transmitted by secreted polypeptides (e.g., mitogenic factors, survival factors, cytotoxic factors, differentiation factors, neuropeptides, and hormones) which are in turn received and interpreted by diverse cell receptors. These secreted polypeptides or signaling molecules normally pass through the cellular secretory pathway to reach their site of action in the extracellular environment.

The targeting of both secreted and transmembrane proteins to the secretory pathway is accomplished via the attachment of a short, amino-terminal sequence, known as the signal peptide or signal sequence (von Heijne (1985) *J. Mol. Biol.* 184:99–105; Kaiser & Botstein, (1986), *Mol. Cell. Biol.* 6:2382–2391). The signal peptide itself contains several elements necessary for optimal function, the most important of which is a hydrophobic component. Immediately preceding the hydrophobic sequence is often a basic amino acid or acids, whereas at the carboxyl-terminal end of the signal peptide are a pair of small, uncharged amino acids separated by a single intervening amino acid which defines the signal peptidase cleavage site. While the hydrophobic component, basic amino acid and peptidase cleavage site can usually be identified in the signal peptide of known secreted proteins, the high level of degeneracy within any one of these elements makes difficult the identification or isolation of secreted or transmembrane proteins solely by searching for signal peptides in DNA data bases (e.g. GeneBank, GenPept), or based upon hybridization with DNA probes designed to recognize cDNA's encoding signal peptides.

Secreted and membrane-bound cellular proteins have wide applicability in various industrial applications, including pharmaceuticals, diagnostics, biosensors and bioreactors. For example, most protein drugs commercially available at present, such as thrombolytic agents, interferons, interleukins, erythropoietins, colony stimulating factors, and various other cytokines are secretory proteins. Their receptors, which are membrane proteins, also have potential as therapeutic or diagnostic agents. Significant resources are presently being expended by both industry and academia to identify new native secreted proteins.

According to a screening method recently reported by Klein et al. (1996), *Proc. Natl. Acad. Sci.* 93:7108–7113 and Jacobs (U.S. Pat. No. 5,563,637, issued Jul. 16, 1996), cDNAs encoding novel secreted and membrane-bound mammalian proteins are identified by detecting their secretory leader sequences using the yeast invertase gene as a reporter system. The enzyme invertase catalyzes the breakdown of sucrose to glucose and fructose as well as the breakdown of raffinose to sucrose and melibiose. The secreted form of invertase is required for the utilization of sucrose by yeast (*Saccharomyces cerevisiae*) so that yeast cells that are unable to produce secreted invertase grow poorly on media containing sucrose as the sole carbon and energy source. Both Klein, supra, and Jacobs, supra, take advantage of the known ability of mammalian signal sequences to functionally replace the native signal sequence of yeast invertase. DNA from a mammalian cDNA library is ligated to the 5'-end of a DNA encoding a nonsecreted yeast invertase (e.g., lacking the natural invertase signal peptide), the ligated DNA is isolated and transformed into yeast cells that do not contain an invertase gene. Recombinants containing the nonsecreted yeast invertase gene ligated to a mammalian signal sequence are identified based upon their ability to grow on a medium containing only sucrose or only raffinose as the carbon source. The mammalian signal sequences identified are then used to screen a second, full-length mammalian cDNA library to isolate the full-length clones encoding the corresponding secreted proteins.

Given the great efforts presently being expended to discover novel secreted and transmembrane proteins as potential therapeutic agents, there is a great need for an improved system which can simply and efficiently identify the coding sequences of such proteins in mammalian recombinant DNA libraries. While effective, the invertase yeast selection process described above has several disadvantages. First, it requires the use of special yeast cells in which the SUC2 gene encoding the invertase protein has been deleted or the coding sequence of the native invertase signal has been mutated so that the invertase is not secreted. Second, even invertase-deficient yeast may grow on sucrose or raffinose, albeit at a low rate, therefore, the invertase selection may need to be repeated several times to improve the selection for transformants containing the signal-less yeast invertase gene ligated to a mammalian secretory leader sequence. See, Jacobs, supra. Third, the invertase selection process is further inadequate because a certain threshold level of enzyme activity needs to be secreted to allow growth. Although 0.6–1% of wild-type invertase secretion is sufficient for growth, certain mammalian signal sequences are not capable of functioning to yield even this relatively moderate level of secretion (Kaiser et al. (1987), *Science* 235:312–317). As a result, there still exists the need for an improved and simplified technique for selecting genes encoding signal sequence-containing (secreted or membrane-bound) polypeptides.

SUMMARY OF THE INVENTION

The present invention concerns a novel and improved method for identifying genes encoding secreted and membrane-bound proteins using a host phenotypic background that is deficient in post-translational translocation of siren sequences, sequences that, as discovered herein, are functionally, but not structurally similar, to authentic signal peptides. Siren sequences in their native context are not authentic signal sequences, but nonetheless direct secretion of a C-terminally attached reporter protein, resulting in false positives that lead the gene searcher astray during a search for DNA encoding novel secreted proteins. These misleading sequences, reminiscent of the mythical creatures ("sirens") that led mariners astray, have been termed "siren sequences." As discovered herein, the siren sequences allow secretion of the attached reporter protein via a post-translational translocation pathway, not a co-translational secretion pathway. It has been further discovered herein that when screening or selecting for heterologous-signal-peptide-directed reporter protein secretion using yeast deficient for translocating siren-sequence/reporter protein fusion constructs, a significant number of false positives are thereby eliminated. The present methods thus provide a greater relative number of correctly identified signal sequences, minimizing the cost and time required to identify and characterize non-novel or false sequences.

Yeast cells deficient in the post-translational translocation pathway, but that still retain co-translational pathway secretion, are a preferred host for transformation with DNA containing a coding sequence of a mammalian peptide ligated to DNA encoding the reporter protein lacking a functional native signal peptide. The transformed cells are selected or preferably screened for their ability to secrete the reporter protein. The DNA encoding the signal sequence/reporter protein, in the yeast cells that were identified as positive for reporter secretion, is then analyzed for novelty, by comparison to sequences in gene or protein databanks for example. The DNA encoding the signal sequence/reporter protein is optionally isolated, and preferably purified. A full-length cDNA or genomic DNA corresponding to identified novel DNA can be isolated by means known in the art.

Preferably, the yeast cell comprises a siren-sequence post-translational translocation deficient allele of a gene encoding a post-translational translocation pathway protein. A translocation-deficient sec71 allele, sec72 allele, or sec62 allele is preferred, more preferably the truncated sec71 allele of SEQ ID NO: 8. Other methods can be used to create a suitable post-translational translocation deficiency in yeast, including but not limited to an antisense molecule to a nucleic acid encoding a protein in the post-translational translocation pathway, such as SEC61p, SEC72p, or SEC62p, or other proteins implicated in this pathway such as SEC63p, YDJ1p, or heat shock protein genes SSA1p thru 4p. Chemicals or ligands that interfere with the translocation mediated by these proteins or the complex-formation of these proteins can be used to affect the host yeast cells. Alternatively, the yeast can have a mutation in a regulatory gene that controls transcription or translation of the post-translational translocation pathway genes. For best efficiency the translocation deficiency is non-reverting, by using an allele encoding a truncated sec71 protein for example. *Saccharomyces cerevisiae* is a preferred yeast. Methods for making these host cells are also provided.

In a most preferred embodiment a starch degrading enzyme is used as the reporter molecule. Preferably, this reporter molecule is amylolytic. More specifically, according to the present invention mammalian signal sequences are detected based upon their ability to effect the secretion of a starch degrading enzyme (e.g. amylase) lacking a functional native signal sequence. The secretion of the enzyme is monitored by the ability of the transformed yeast cells, which cannot degrade starch naturally or have been rendered unable to do so, to degrade and assimilate soluble starch. Most preferably, the method employs amylase as the reporter protein, the non-transformed yeast cells are non-amylolytic, and the transformed cells are then screened for amylase secretion by their ability to degrade starch.

In one embodiment, the invention relates to a method of detecting DNA comprising the coding sequence of a mammalian signal peptide which comprises:

a) screening or selecting siren-sequence post-translational-translocation deficient, reporter-gene deficient yeast cells, transformed with DNA obtained by the ligation of said mammalian recombinant DNA library to DNA encoding the reporter protein lacking a functional native signal peptide, for their ability to secrete the reporter protein; and b) determining whether the mammalian DNA in the yeast of step (a) is novel.

The identified DNA is optionally isolated and purified. Preferably, screening of non-amylolytic yeast cells, transformed with DNA containing the coding sequence of a mammalian signal peptide ligated to DNA encoding an amylase lacking a functional native signal peptide, for their ability to degrade starch is performed. The yeast cells are preferably cells of a *Saccharomyces cerevisiae* strain, more preferably lacking a native amylolytic enzyme, and containing an auxotrophic marker suitable for the selection of plasmid maintenance following transformation. The mammalian coding sequence is inserted amino terminal to, and in-frame with the secretion defective reporter gene. In a particularly preferred embodiment, the ATG start codon is eliminated or mutated at the N-terminus of the signal sequence as well as at the N-terminus of the mature reporter gene, such that translation is initiated only from the start codon of the mammalian signal peptide to be identified. Preferably the reporter gene is amylase, less preferably the reporter gene is invertase.

In another embodiment, the invention relates to a method of detecting, in a mammalian recombinant DNA library, DNA encoding a secreted or transmembrane protein or an N-terminal fragment thereof, which comprises:

a) screening or selecting siren-sequence post-translational-translocation deficient, reporter-gene deficient yeast cells, transformed with DNA obtained by the ligation of said mammalian recombinant DNA library to DNA encoding the reporter protein lacking a functional native signal peptide, for their ability to secrete the reporter protein; and b) determining whether the mammalian DNA in the yeast of step (a) is novel.

The identified DNA is optionally isolated and purified. The yeast is preferably a *Saccharomyces cerevisiae* strain, or another yeast strain lacking a native reporter gene, most preferably an amylase gene, while the recombinant DNA library preferably is a mammalian cDNA library. The DNA identified preferably is a full-length cDNA encoding a novel secreted or transmembrane polypeptide. The DNA ligated to the reporter gene is preferably obtained by the ligation of a mammalian cDNA library enriched for signal sequences. The cDNA identified as able to direct secretion of the reporter protein can be analyzed to determine novelty.

In further embodiments yeast cells which can naturally degrade starch can be employed, provided that the native amylase signal sequence has been rendered inoperable or preferably deleted prior to the ligation of the mammalian recombinant DNA library.

In yet further embodiments of the above methods the screening method is selected from growth on selective media followed by replica plating onto YEPD-starch media, growth on selective media wherein starch is directly incorporated, and growth on selective media wherein starch bonded to a visible dye is directly incorporated. Less preferably the reporter gene is invertase and the transformed yeast cells are selected for their ability to grow on sucrose or raffinose.

Since known, previously identified signal sequences have been observed to reoccur in the screens or selections described herein, PCR or other methods can be used to rapidly identify positive yeast bearing these known sequences, thus avoiding subsequent isolation and characterization of these frequently occurring non-novel cDNAs.

BRIEF DESCRIPTION OF THE DRAWINGS

FIG. 1 represents pSST-amy.1, a yeast expression vector or plasmid preferably employed with the invention.

FIG. 2 represents diagrammatically a comparison between the yeast screening process of the invention and the invertase selection process of the prior art.

FIG. 3 represents diagrammatically the preferred embodiment encompassing the method for creating an enriched c-DNA library.

FIG. 4 represents the amino acid sequence of the fusion protein RS20-AMY (SEQ ID NO: 4), with the N-terminal sequence of the S20 protein (human ribosomal protein s20; GenBank accession L06498) fused to murine α-amylase as shown, with an intervening Kex2p processing site.

FIG. 5 presents a hydropathy plot for RS20-AMY amino acid sequence, using a 20 amino acid window. The algorithm of Kyte and Doolittle ("A simple method for displaying the hydropathic character of a protein," *J. Mol. Biol.* 157:105–132 (1982)) was used to generate this and other hydropathy plots herein.

FIG. 6 presents the protein sequence of the RL15-AMY fusion (SEQ ID NO: 5), with the N-terminal being from the 3'-UTR sequence from human ribosomal protein 115 (GenBank accession L25899).

FIG. 7 presents a hydropathy plot for the RL15-AMY amino acid sequence.

FIG. 8 presents the protein sequence of the PERT-AMY fusion (SEQ ID NO: 6). The N-terminal is from human thyroperoxidase (GenBank accession Y00406), a known secreted protein with a bona-fide signal sequence.

FIG. 9 presents a hydropathy plot for the PERT-AMY amino acid sequence.

FIG. 10 presents the protein sequence of wild-type Sec71p (SEQ ID NO: 7) and mutant truncated Sec71p (SEQ ID NO: 8) from strain DQY205-3.

FIGS. 11A–D present a comparison of the nucleic acid sequences of wild-type Sec71 (phB; SEQ ID NO: 9) and mutant sec71 alelle (phE3; SEQ ID NO: 10). The sequences differ by the insertion of base "A" at 884 of phE3, to yield a frameshift that results in the truncated protein.

SEQ ID NO: 1 is the nucleotide sequence represented by the expression plasmid of FIG. 1. SEQ ID NO:2 is the forward oligonucleotide primer used in the PCR amplification of Example 3. SEQ ID NO:3 is the reverse oligonucleotide primer used in the PCR amplification of Example 3. SEQ ID NO: 4 is the amino acid sequence of the RS20_AMY fusion of FIG. 5. SEQ ID NO: 5 is the amino acid sequence of the RL15_AMY fusion of FIG. 6. SEQ ID NO: 6 is the amino acid sequence of the PERT_AMY fusion of FIG. 8. SEQ ID NO: 7 is the amino acid sequence of wild-type Sec71p shown in FIG. 10. SEQ ID NO: 8 is the amino acid sequence of the mutant Sec71p (truncation mutation) in strain DQY205-3, as shown in FIG. 10. SEQ ID NO: 9 is the nucleic acid sequence of wild-type Sec71p shown in FIG. 11. SEQ ID NO: 10 is the nucleic acid sequence of the mutant Sec71p (truncation mutation) in strain DQY205-3, as shown in FIG. 11.

DETAILED DESCRIPTION OF THE INVENTION

Definitions

Terms employed throughout this application should be construed with their ordinary and common meanings as known to those of ordinary skill in the art. Additionally, Applicants desire that the following terms be given the following construction:

The terms "signal sequence," "signal peptide," and "secretory leader" are used interchangeably and refer to a short (usually about 15–60 amino acids), continuous stretch of amino acids at the amino-terminus of secreted and membrane-bound polypeptides, which directs their delivery to various locations outside the cytosol. Thus, specific sorting or targeting signals, which include signal sequences, may direct the delivery of polypeptides into the nucleus, ER, mitochondria, peroxisomes, etc. Signal sequences usually contain a hydrophobic core of about 4–15 amino acids, which is often immediately preceded by a basic amino acid. At the carboxyl-terminal end of the signal peptide there are a pair of small, uncharged amino acids separated by a single intervening amino acid that defines the signal peptide cleavage site (von Heijne, G. (1990) *J. Membrane Biol.;* 195–201). Despite their overall structural and functional similarities, native signal peptides do not have a consensus sequence.

The term "siren sequence," "siren peptide," and "siren leader" are used interchangeably and refer to a short (usually about 15–60 amino acids), continuous stretch of amino acids that function as a signal peptide when placed at the N-terminus of a reporter protein, but are not authentic signal sequences from naturally-occurring secreted and membrane-bound proteins. Siren sequences lead to false positives in the screening and selecting methods designed to identify signal sequences from novel secreted or membrane proteins. As determined herein, siren sequences fused N-terminal to a reporter protein allow secretion of the reporter via a post-translational translocation pathway. Preferred siren sequences for testing and identifying post-translational translocation deficient yeast are in SEQ ID NO: 4 (the sequence in RS20__AMY fusion of FIG. 5) or in SEQ ID NO: 5 (the sequence in RL15__AMY fusion of FIG. 6). Siren sequences are typically not hydrophobic.

The term "amylase" is used to refer to an amylolytic enzyme catalyzing the hydrolysis of α- D-glucosidic linkages of polysaccharides such as starch. The term specifically includes endoamylases (a.k.a. α-amylases), which are responsible for endohydrolysis of α-1,4-D-glucosidic bonds at random; exoamylases, which attacks the α-1,4-D-glucosidic linkages only from the non-reducing outer polysaccharide ends; β-amylases, which break every alternate glucosidic bond to produce maltose; and glucoamylases (a.k.a. γ-amylases), which hydrolyze terminal α-1 ,4-D-glucosidic linkages to produce β-D-glucose, and sometimes also α-1,6-D-glucosidic bonds (Modenaetal. (1986),*Arch. Bioch. Biophys* 248:138–150. The source of the amylase enzymes used in the present invention can be of any source, including enzymes of mammalian, e.g. human, bacterial, fungal, or plant origin, whether purified from natural sources, prepared by recombinant DNA technology, chemical synthesis or any combination of these and/or other techniques. The term "amylase", unless otherwise indicated, collectively refers to all amylases covered by this definition. Amylases are commercially available, or can be produced by conventional methods well known for those skilled in the art. The most commonly known α-amylases are those isolated from various mammalian sources, including, e.g., human saliva, human, mouse (murine), hog and rat pancreas, *Bacillus subtilis*, *Bacillus coagulans*, *Bacillus amyloliquefaciens*, *Bacillus licheniformis*, *Bacillus stearothermophilus*, various Aspergillus strains (e.g., *Aspergillus, awamori*), *Pseudomonas saccharophila*, *Streptomyces hygroscopicus*, *Streptomyces venezuelae*, *Streptomyces limosus*, *Schwanniomyces occidentalis*, *Saccharomycopsis fibuligera*, *Drosophila melanogaster*, *Saccharomyces diastaticus* and barley malt. *Saccharomyces cerevisiae* also produces an intracellular glucoamylase, which can be used with the present invention, but this enzyme is only produced by diploid cells undergoing sporulation. The nucleotide sequences of the human salivary and pancreatic α-amylase genes have, for example, been disclosed by Nakamura et al. (1983), *Gene* 28, 263–270, and Nishide et al. (1986) *Gene* 50, 371–372. The cloning of the α-amylase cDNA of *Aspergillus shirousamii* has been reported by Shibuya et al. (1992) *Biosci. Biotech Biochem.* 56, 174–179. The cloning of a glucoamylase from the same organism was first described in Shibuya et al. (1990) *Agric. Biol. Chem.*, 54, 1905–1914. The cloning of a glucoamylase gene of the yeast *Arxula adeninivorans* from a genomic library is reported by Bui et al. (1996), *Appl. Microbiol. Biotechnol.* 44, 610–619. Potato α-amylase genes are disclosed, for example, in U.S. Pat. No. 5,498,832, issued Mar. 12, 1996. The genes specifically mentioned are for illustration only. A large variety of additional amylase genes has been cloned and sequences from various sources, and further genes can be readily identified by similar techniques. All amylases contain a short, N-terminal signal sequence which directs their secretion. The amylase gene used in accordance with the present invention preferably is of mouse origin or is from an amylolytic yeast. (see, e.g. McCann and Barnett (1986) *Yeast* 2, 109–115).

The phrase "non-amylolytic" is used to refer to yeast cells that do not produce native amylase or in which the signal sequence(s) of the amylase(s) naturally produced has/have been deleted or inactivated, such that the native amylase is not secreted. In contrast, "amylolytic" yeast are those that can degrade starch due to the presence of one or more native secreted amylase enzymes. A typical, and preferred, representative of yeast that cannot degrade starch naturally is *Saccharomyces cerevisiae* (Baker's yeast). Many genes from bacteria, filamentous fungi and yeasts that encode amylolytic enzymes have been cloned into, and expressed in, *S. cerevisiae*. Representatives of other yeast strains lacking native amylase genes and which can be used with the present invention are *Schizosaccharomyces pombe*, *Hansenula polymorpha*, *Kluveromyces lactis* and *Pichia pastoris*. Clementi, R. & Rossi, J. (1986) *Antonie van Leeuwenhoek* 52; 343–352.

The phrase "recombinant DNA library" is used to refer collectively to genomic and cDNA libraries. Preferably, a "recombinant DNA library" contains a substantially complete representation of all genomic or cDNA sequences from a particular cell or tissue source.

The term "DNA" is used to refer collectively to genomic DNA and cDNA, prepared from any source, including bacteria, plant cells, and mammalian cells, preferably cells of high primates, most preferably humans.

The term "plate" is used to refer to petri dishes or 96-well micro titer dishes filled with solid medium used to grow separated bacterial colonies or plaques. The terms "plating" or "plating out" refer to the placement of bacteria, phages or yeast on plates so that colonies or plaques are formed.

"Transformation" means introducing DNA into an organism so that the DNA is replicable, either as an extrachromosomal element or chromosomal integrant. Transformation is usually performed by the $CaCl_2$ transfection (Mandel and Higa, *J. Mol. Biol.* 53, 159–162 (1970)), electroporation (Miller et al., *Proc. Natl. Acad. Sci. USA* 85, 856–860 (1988), Shigekawa and Dower, *BioTechnique* 6, 742–751 (1988)), Ausubel et al., *Current Protocals in Molecular Biology*, Unit 9.3, John Wiley & Sons, Inc. (1995). DEAE-dextran technique (eukaryotic cells, Lopata et al., *Nucleic Acids Res.* 12, 5707 (1984)), and liposome-mediated transfection (Felgner et al., *Proc. Natl. Acad. Sci. USA* 84, 7413–7417 (1987)). Unless otherwise provided, the method used herein for transformation of *E. coli* is electroporation.

"Polymerase Chain Reaction" or "PCR" is a rapid procedure for in vitro enzymatic amplification of a specific DNA segment. The DNA to be amplified is denatured by heating the sample. In the presence of DNA polymerase and excess deoxynucleotide triphosphates, oligonucleotides that hybridize specifically to the target sequence prime new DNA synthesis. One round of synthesis results in new strands of indeterminate length which, like the parental strands, can hybridize to the primers upon denaturation and annealing. The second cycle of denaturation, annealing and synthesis produces two single-stranded products that together compose a discrete double-stranded product, exactly the length between the primer ends. This discrete product accumulates exponentially with each successive round of amplification. Over the course of about 20 to 30 cycles, many million-fold amplification of the discrete fragment can be achieved. PCR protocols are well known in the art, and are described in standard laboratory textbooks, e.g. Ausubel et al., supra, Unit 15.

"Reporter molecule" is a gene which codes for a protein which possesses a unique enzymatic ability or is otherwise easily distinguishable from the mixture of intra- or extracellular proteins, for example by its immunological property. Typically, they are operably linked to test DNA, the transcriptional capability of which can then be estimated from the in vitro activity of the reporter gene product in the culture medium. Reporter genes and their application to mammalian gene transcription are described by Alain and Cook, (1990), *Anal. Biochem.* 188: 245–284. A reporter molecule in the present invention is testing transcription, translation, and secretory competence. In the present invention, the preferred reporter molecule is a starch degrading enzyme, which is most preferably amylase.

Detailed Description

The methods of the present invention are preferably used for screening recombinant DNA libraries for the presence of novel secreted or membrane-bound proteins.

The first step in secretion of eukaryotic proteins include targeting and translocation of nascent polypeptide chains across the endoplasmic reticulum membrane ("ER"). At least two pathways are known. In the "co-translational pathway" targeting to the membrane is catalyzed by the signal recognition particle (SRP) and is carried outbyamultisubunitcomplex termed the translocon or Sec61p complex. The translocation event is co-translational—the SRP binds a signal sequence of the nascent chain emerging from the ribosomal complex, pauses translocation, and the SRP is in turn bound by the ER membrane-bound SRP receptor attached to the translocon. This co-translational, SRP-dependent pathway is common to both yeast and mammalian cells. The co-translational pathway is believed to be mediated by at least two independent, but structurally related, membrane bound complexes: a Sec61p complex that exists in a trimeric complex of Sec61p, Sbh1p and Sss1p; and a trimeric Ssh1p complex of Ssh1p, Sbh2p, and SSs1p.

Either or both can be used by the cell to achieve co-translational translocation across the ER membrane.

A post-translational, SRP-independent translocation pathway also exists in yeast. This is believed mediated by a heptameric Sec complex of the Sec61p complex associated with the Sec62-Sec63p complex, which comprises Sec62p, Sec63p, Sec71p, and Sec72p (Fang and Green, "Nonlethal sec71-1 and sec72-1 mutations eliminate proteins associated with the Sec63p-BiP complex from *S. cerevisiae,*" *MolBiol. Cell.* 5:933–942 (1994); Feldheim and Scheckman, "Sec72p contributes to the selective recognition of signal peptides by the secretory polypeptide translocation complex,"*J. Cell Biol.* 126:935–943 (1994)). The Sec62-Sec63p protein complex functions in post-translation translocation and in the process of karyogamy during yeast cell mating (Kaiser et al., "Protein secretion, membrane biogenesis, and endocytosis," In: Pringle, J. R., Broach, J. R. and Jones, E. W. (Eds.), *The Molecular and Cellular Biology of the Yeast Saccharomyces: Cell Cycle and Cell Biology,* Cold Spring Harbor Laboratory Press, pp.91–227 (1997)). This complex associates with Kar2p (BiP), which is associated with the luminal side of the ER and increases translocation efficiency. The Ssh1p complex has not been found associated with the Sec62-Sec63p complex. The Sec61p complex has been shown to form an oligomeric ring in the membrane, which provides a pore through which proteins pass (Schekman, "Peptide Translocation: A Pretty Picture is Worth a Thousand Words," *Cell* 87:593–595 (1996); Hanein et al. "Oligomeric Rings of the Sec61p Complex Induced by Ligands Required for Protein Translocation," *Cell* 87:721–732 (1996)). This pore-forming complex associates with either the SRP-dependent proteins for co-translational translocation or the Sec62-Sec63p complex for post-translational translocation. The Sec71p and Sec72p were reported as non-essential to the post-translational translocation pathway since null mutants in either showed only a partial SRP-independent translocation defect and such yeast were viable, whereas Sec62p and Sec63p were found to be essential for this pathway while not essential for yeast viability. However, a role for Sec63p and Kar2p in the co-translational pathway has been suggested (Brodsky et al. *Proc. Natl. Acad. Sci* 92:9643–9646 (1995)). Ng et al. (*J. Cell Biol.* 134:269–278 (1996)), after a determination of hydrophobicity of signal sequences from only a few translocated proteins, suggested that signal sequences that direct to the SRP-dependent pathway (or to both pathways) are more hydrophobic than hydrophobic signal sequences that direct proteins only to the post-translational translocation pathway. While not to be limited by any one theory, the present discovery of the loss of halo mutant genotype as described in the Examples is consistent with the notion that the post-translational translocation pathway is being utilized for the transport of siren-reporter fusion proteins, presumably out of the cytoplasm and into the secretory pathway. Other organisms for which a post-translational pathway is known now or in the future, such as for Bacillus or *E. coli,* and which can use mammalian signal peptide as secretion signals, can be used in the present invention.

In the present methods genes encoding novel secreted and membrane-bound proteins are identified by identifying their signal peptides that have fused to a reporter gene to enable the host cell to secrete the reporter protein. As taught herein, using a host phenotypic background that is deficient in post-translational translocation of siren sequences, which are functionally, but not structurally, similar to signal peptides provides an improved method of novel protein identification. Siren sequences are not authentic signal sequences, but nonetheless direct secretion of an attached reporter protein, resulting in false positives that consume time and resources in subsequent isolation and characterization of the identified DNAs. When screening or selecting for heterologous-signal-peptide directed reporter protein secretion using yeast deficient in translocating siren-sequence/reporter protein fusion constructs, a significant number of false positives are thereby eliminated. As discovered herein, the siren-sequences allow secretion of the attached reporter protein via a post-translational translocation pathway, not a co-translational secretion pathway. Yeast cells deficient in the post-translational translocation pathway, but that still retain co-translational pathway secretion, are an improved host for transformation with DNA containing a coding sequence of a mammalian signal peptide ligated to DNA encoding the reporter protein lacking a functional native signal peptide. The transformed cells are then selected or preferably screened for their ability to secrete the reporter protein. The mammalian DNA, contained in the yeast cells that were identified as positive for reporter secretion, is then analyzed for whether it is novel or derived from a novel, mammalian gene encoding a secreted or membrane-bound protein. The DNA encoding the signal sequence/reporter protein can be isolated, preferably purified, prior to analysis if desired. Typically, a host yeast cell will contain a siren-sequence post-translational translocation deficiency, a reporter protein deficiency, and a selectable plasmid-maintenance-marker-deficiency. The transformed yeast cell for screening or selection that further includes a plasmid comprising a selectable marker for plasmid maintenance that complements the selectable plasmid-maintenance-marker-deficiency and a mammalian peptide-reporter protein fusion gene that complements the reporter protein deficiency.

The present compositions (host cells) and methods are particularly useful in searching cDNA libraries prepared from tissues which remain uncharacterized or poorly characterized for secreted proteins.

Preferably, the host yeast cell comprises a siren-sequence post-translational translocation deficient allele of a gene encoding a post-translational translocation pathway protein. These proteins include those in the Sec62-Sec63 complex, BiP, or other proteins implicated in this pathway such as YDJ1, or heat shock protein genes SSA1 thru 4. A translocation-deficient sec71 allele, sec72 allele, or sec62 allele is preferred, with the truncated sec71 allele of SEQ ID NO: 8 as in DQY140 being more preferred. The sec71 and sec72 alleles from strains sec71-4, sec71-16, sec72-43, HWY9, HWY30, HWY4, HWY5, and HWY6 are useful to practice the invention, as indicated in the Examples. Useful alleles will have the phenotype described herein, particularly the selective loss of halo phenotypes demonstrated in the Examples when in a yeast strain transformed with the reporter plasmids, tested and scored in the assays illustrated in the Examples. A preferred phenotype of halo loss is one similar to that observed for a strain bearing the truncated sec71 allele (SEQ ID NO:8) from DQY140 (see Table 3). Other methods can be used to create a post-translational translocation deficiency in yeast. The yeast can express an antisense molecule to a nucleic acid encoding a protein in the post-translational translocation pathway, or other proteins implicated in this pathway, to reduce expression of the targeted protein. The yeast can be treated with chemicals or ligands (or recombinantly express ligands) that interfere with the translocation mediated by post-translational translocation pathway proteins or the formation of the translocation complex. The yeast can contain mutations in regulatory genes that control transcription or translation of the post-translational translocation pathway genes. Conditions or mutations that provide a suitable post-translational translocation deficiency are readily identified as secreting a known signal peptide fusion protein but secreting a siren sequence reporter fusion at a reduced rate or not at all. The reporter fusions taught in the examples herein are readily employed to characterize conditions or mutations for use in the invention. For best efficiency in the screening and selecting methods, the translocation deficiency is non-reverting, for example, by using an allele encoding a truncated sec71 protein. Suitable yeast are those for which transformation systems and reporter plasmids are available or can be obtained, e.g Schizosaccharomyces, Hansenula, Kluveromyces, Pichia, and Saccharomyces. *Saccharomyces cerevisiae* is a preferred yeast.

The host yeast cell can be made by introducing into the genome of a yeast cell a reporter protein deficiency, a selectable plasmid-maintenance-marker-deficiency, and a siren-sequence post-translational translocation deficiency using known methods and those taught herein. The deficiencies can be introduced using well known yeast genetic techniques and genes, yeast gene replacement techniques (Rothstein, R. *Methods Enzymol.* 194:281–301 (1991)), or yeast recombinant DNA methods, such as antisense expression, or treating the host cell with appropriate compounds or ligands. A siren-sequence post-translational translocation deficient allele of a gene encoding a post-translational translocation pathway protein can be introduced into an appropriate genetic background, for example, by mating to yield a diploid, by mating and sporulation to yield haploids, or by homologous gene replacement or disruption. The siren-sequence post-translational translocation deficient allele can be readily obtained from a loss of halo screen using a siren-sequence/reporter gene fusion as taught herein or by using the sec71 allele provide herein.

A reporter protein is one that can be secreted when attached to a signal peptide, and is one whose secretion is readily identified. Reporter secretion is most readily identified by its enzymatic activity or by its immunological activity. A reporter protein is preferably not native to the host cell. If native, the native copy of its gene should be inactivated. Melibiase can be used as a reporter protein using the overlay assay described by Post-Beittenmiller et al. ("Regulation of basal and induced levels of the MEL1 transcript in *Saccharomyces cerevisiae*,"Mol. Cell. Biol.4 (7):1238–45 (1984)). The MEL1 gene encodes alpha-galactosidase necessary for the catabolism of melibiose. A chromogenic substrate allows ready detection of yeast that secrete melibiase. The invertase system described by Jacobs (U.S. Pat. No. 5,563,637) can be used. However, in a most preferred embodiment a starch degrading enzyme is used as the reporter molecule. Preferably, this reporter molecule is amylolytic. More specifically, according to the present invention mammalian signal sequences are detected based upon their ability to effect the secretion of a starch degrading enzyme (e.g. amylase) lacking a functional native signal sequence. The secretion of the enzyme is monitored by the ability of the transformed yeast cells, which cannot degrade starch naturally or have been rendered unable to do so, to degrade soluble starch.

In one embodiment, invertase is the reporter for a selection based on secretion of invertase activity. A cDNA encoding a secreted protein can be identified by the method containing the steps: a) constructing a cDNA library from cellular messenger RNA; b) ligating said cDNA library to a DNA encoding a nonsecreted yeast invertase from which the secretory leader sequence and initiating methionine have been deleted; c) transforming the DNA of step b) into a yeast cell which does not contain an invertase gene and which is siren-sequence post-translational translocation deficient; d) selecting transformed yeast cells from step c) which are capable of growth on sucrose or raffinose; e) analyzing the DNA for novelty, and optionally, purifying DNA from the yeast cells of step, analyzing the DNA obtained to determine its sequence, preparing a second cDNA library from cellular messenger RNA, and screening said second cDNA library to detect full-length cDNAs which contain the sequence of step; and isolating the full-length cDNA wherein the isolated cDNA encodes a putative secreted protein. In another embodiment, the method is modified by preparing the ligated constructs from bacteria by the steps of: transforming the ligated DNA into bacteria; isolating DNA containing cDNA ligated to the DNA encoding the nonsecreted yeast invertase from the transformed bacteria of step 1); wherein said additional steps are performed after step b) and before step c), and wherein the DNA isolated in step 2) is used for the transformation in step c). A preferred bacteria is *E. coli*. Preferably, either the first codon encoding the mature invertase protein is deleted or the first two codons encoding the mature invertase protein are deleted. The preferred cellular messenger RNA is mammalian cellular messenger RNA. In another embodiment using invertase reporter, the steps include: a) constructing a cDNA library from mammalian cellular RNA; b) ligating said cDNA library to a DNA encoding a nonsecreted yeast invertase; c) transforming the ligated DNA into *E. coli*; d) isolating DNA containing mammalian cDNA ligated to the DNA encoding the nonsecreted yeast invertase from the transformed *E. coli* of step c); e) transforming the DNA of step d) into a yeast cell which does not contain an invertase gene and which is siren-sequence post-translational translocation deficient; f) selecting yeast cells capable of growth on sucrose or raffinose; g) purifying DNA from the yeast cells of step f); h) analyzing the DNA obtained from step g) to determine its sequence and to determine whether it contains a novel sequence; I) screening a second cDNA library to detect a full-length cDNA which contains the novel sequence of step h); j) isolating the full-length cDNA of step I) wherein the isolated cDNA encodes a putative secreted mammalian protein. Optionally, the DNA of step (f) can be analyzed for novelty prior to or without purification, for example by using PCR techniques.

While the invertase reporter selection system can be used, a most preferred embodiment uses a starch degrading enzyme as the reporter molecule. Starch is one of the most widely distributed, naturally occurring organic compound which is derived mainly from higher plants. Soloman, B. (1978) *Advances in Biochemical Engineering*, eds., Springer Berlin Heidelberg, New York, 135–177. Starch comprises two major components: (1) amylose, which comprises mainly $\alpha$-1,4-linked D-glucose residues; and (2) amylopectin, which comprises both $\alpha$-1,4-and $\alpha$-1,6-linked D-glucose residues. Jensen B. F. and Norman B. (1984), *Process Biochem.* 19:129–134. The relative content of amylose and amylopectin in starch varies with the source. Amylose generally accounts for 20%–30% of the starch weight and has an average chain length of 500–1000 glucose units. Manners, D. J. (1989), *Carbohydr. Pol.* 11:87–112. Amylopectin represents the major fraction of starch (70%–80%) and usually has a bimodal pattern of distribution, with shorter chains having average lengths of 11–25 and the longer chains 40–60D-glucosyl residues, Soloman, supra. In a preferred embodiment of the invention, the means of screening uses starch because starch can be broken down into its various component parts by the operation of amylase, and the presence of starch (or lack thereof) can be made readily discernable to the naked eye.

The construction of a genomic DNA library typically includes the following steps: (1) isolation of genomic DNA, (2) partial or complete digestion of the DNA, and (3) size fractionation. The DNA is then ligated to a vector, and introduced into a host cell, e.g. *E. coli* (by transformation with a plasmid vector or by in vitro packaging into bacteriophage particles and subsequent infection of *E. coli*). The latter steps are substantially the same for genomic and cDNA libraries. The size of a library of random genomic DNA fragments that is required to ensure representation of all sequences present in the genome will depend on the size of the genome and the size of the cloned fragments (see, Clark and Carbon, *Cell* 9, 91–99 (1976)). There are a number of different procedures for the preparation of genomic DNA, all of which start with some form of cell lysis, followed by deproteinization and recovery of the DNA. Typical protocols for the preparation of genomic DNA from mammalian, plant tissues and bacteria are described, e.g. in Ausubel et al, supra, Units 2.2–2.4. Digestion of the genomic DNA is performed by restriction enzymes, following routine procedures of partial or complete digestion. In order to avoid distortions, it is important to select an enzyme that cuts the DNA with high frequency but without any bias in selection of one site over another. A partial digestion method for the maximization of the randomness of DNA sequence in genomic libraries is described, for example, in Seed et al., *Gene* 19, 201–209 (1982). Protocols for enzymatic manipulation of DNA are disclosed in Ausubel et al., supra, Unit 3. The completely or partially digested DNA must then be size fractionated to remove small and large fragments, which would interfere with subsequent cloning. Methods for size fractionation are well known in the art and are typically based on sucrose gradient fractionation or preparative gel electrophoresis. The DNA is then ligated into a vector, which is introduced into a host cell, typically *E. coli*. General techniques for the construction of genomic DNA libraries are disclosed, for example, in Ausubel et aL, supra, especially in Units 5.1.1–5.1.2; 5.3.2–5.3.6; 5.4.1–5.4.3; and 5.7.1–5.7.3. Introduction of the library into *E. coli* can be performed by any standard transformation techniques, including $CaCl_2$ transfection, and electroporation.

In a typical procedure of constructing recombinant cDNA libraries, poly(A)$^+$ mRNAs are isolated from cells, preferably a cell type in which the mRNA encoding the desired polypeptide is produced in large quantities. The mRNAs are then converted into double stranded cDNA (dscDNA) in vitro using the enzyme reverse transcriptase to synthesize complementary cDNA strands from the mRNA template. In order to obtain double-stranded DNA suitable for ligation into a vector, the dscDNA copy of the mRNA is methylated and equipped with suitable (usually EcoRI) linkers. Methods for methylation of DNA are well known in the art, and involve the use of commercially available methylases which covalently join methyl groups to adenine or cytosine residues within specific target sequences. For example, EcoRI methylates an adenine residue within the EcoRI recognition sequence. In the process of converting mRNA into double stranded cDNA in vitro, a first cDNA strand is synthesized by the reverse transcriptase and separated from the rnRNA by treatment with alkali or using a nuclease such as the enzyme RNase H. Conveniently, this step can be achieved using a reverse transcriptase that also has RNase H activity. *E. coli* DNA polymerase then uses the first cDNA strand as a template for the synthesis of the second cDNA strand, thereby producing a population of dscDNA molecules from the original poly(A)$^+$ mRNA. After converting the 5' and 3' ends into blunt ends, the dscDNA can be ligated to linkers/adaptors and subsequently ligated into suitable vectors and transformed or packaged into a cell, thereby forming the library. For methods for preparing high-quality cDNA libraries see, for example, Gubler and Hoffman, *Gene* 25:263–269 (1983); Okayama and Berg, *Mol. Cell. Biol* 2, 161–170 (1982); and Kato et al., *Gene* 150:243–250 (1994). Typical protocols for making cDNA libraries are also described in Ausubel et al., supra, especially in Units 5.2.1; 5.5.2–5.5.7; 5.6.1–5.6.8; and 5.8.1–5.8.11. A particularly advantageous method for converting mRNA into dscDNA is disclosed in U.S. Pat. No. 5,891,637 (and its corresponding application Ser. No. 08/929,967) issued Apr. 06, 1999. According to this method, reverse transcriptase-producing cells are transformed with vectors in which the 5' end of a mRNA molecule having a 5'oligonucleotide cap is ligated to a single-stranded 5' overhang complementary to the oligonucleotide cap, and the 3' end of the mRNA molecule is ligated to a single-stranded 3' overhang complementary to the 3' end of the mRNA molecule, so that the reverse transcriptase produced by the cell converts the mRNAs into dscDNAs to form a cDNA library.

In the preferred embodiment of carrying out the present invention, a library is used which is enriched in signal sequences. This library is enriched in amino terminal signal sequences which are within a cloning vector that possesses both a unique restriction site at the 5' end of the inserted cDNA clone and a DNA promotor 5' to the inserted cDNA. Next, the cDNA clone is transcribed using the corresponding RNA polymerase to create an RNA transcript which contains the sequence of the transcribed cDNA in addition to vector sequence containing the 5' unique restriction sequence. For example, an Sp6 promotor can be used in conjunction with Sp6 polymerase or a T7 promotor with T7 polymerase. Suitable additional promoters and RNA polymerases will be apparent to one of ordinary skill in the art. The RNA sequence is then randomly primed and replicated to produce various single stranded DNA fragments. These fragments are in turn replicated into double stranded fragments and specific DNA adapters are ligated onto the ends of the DNA fragments. The adapters are used in order to convert the blunt end of the replicated terminus into an exposed 5' end, similarly to what would result if a restriction enzyme had been used. Exposed 5' ends are necessary to maximize the efficiency of T4 DNA ligase, an essential step for insertion of the cDNA fragment into the cloning vector. The ligated double stranded fragments are then digested with specificity for cutting at the unique restriction site. The DNA fragments within a defined size range may then be isolated by gel electrophoresis and cloned into restriction sites within the reporter vector, preferably an amylase vector, that are compatible with the specific 5' unique restriction site and the DNA adapter. In this manner it is possible to identify only those DNA fragments which correspond to the 5' end of the initial cDNA within the full length library. These fragments may then be used in the next step, which is the creation of a cDNA fusion library.

In a most preferred embodiment a cDNA library enriched in signal sequences is used which is prepared by (a) creating a full-length cDNA library containing a first unique restriction site and a DNA promotor region 5' to the inserted cDNA; (b) transcribing an mRNA transcript from the cDNA of step a); (c) preparing random DNA oligonucleotide primers and reverse transcribing to create cDNA fragments of the full-length cDNA clone; (d) preparing the cDNA fragments of step c) for ligation, and ligating to an adapter oligonucleotide coding for a second unique restriction site; (e) digesting the cDNA of step d) with a restriction enzyme which cuts at the first unique restriction site; (f) isolating cDNA fragments which have been cut by the restriction enzyme of step (e) and correspond to a size of about 500 to about 1000 base pairs in length; and (g) ligating the isolating cDNA fragment of step f) into reporter expression vector, preferably an amylase expression vector, previously digested with enzymes compatible with the first and second restriction site of the cDNA of step (f).

The use of the above-described enriched signal sequence library offers several advantages. First, this library ensures that all cDNA fragments which are screened or selected in the assay, preferably the amylase assay, as containing signal sequences will be derived from specific cDNA present in the actual full-length library. If the full-length library were created completely independently from the cDNA fragments actually tested in the screen or from the "amylase library," there would be some novel genes identified through chance which were not actually represented in the retained full-length library. As a result, time and effort would be spent not only searching for a clone which doesn't exist in the full-length library, but also in searching a full-length library which actually does contain the gene of interest.

Additionally, the enriched signal sequence library, which contains a population of mammalian cDNA which is enriched in fragments proximal to the 5' end of the cDNA insertion, provides for a greater number of functional signal sequences over that which would be obtained if the tested population were comprised of random cDNA derived from the full length cDNA. The number of selected functional signal sequences is increased because, any signal sequence, if present in the full-length library, will be proximal to the 5' end of the cDNA insertion.

However, despite these enrichment procedures false positives are still encountered. As first identified herein, one family of sequences generating false positives are siren sequences. By using the appropriate host translocation deficient phenotype as taught herein, appearance of siren sequences will be eliminated or minimized.

The next step is the creation of a cDNA-fusion library, in which the library is fused N-terminally to a reporter gene, preferably an amylase gene, lacking a functional signal sequence. The fusion library is created in any suitable yeast cloning vector known in the art, which carries a non-secreted reporter gene, preferably an amylase gene, having its signal sequence deleted or inactivated. Preferably, the vector is derived from a λ phage or a filamentous phage. Vectors derived from a filamentous phage (phagemid vectors) contain an M13, f1 or fd origin of replication. Filamentous phages are very useful cloning vectors because they are suitable for packaging of any length of DNA, and permit the isolation of DNA in either single- or double-stranded form. Prototypes of filamentous phage vectors are M13mp derivatives, that were originally developed by Messing and colleagues. M13-based cloning vectors, along with general techniques for working with them are disclosed, for example, in Messing, *J. Methods Enzymol* 101:20–78 (1983) and Messing et al., *Proc. Natl. Acad. Sci. USA* 74:3642–3646 (1977). Particularly useful M13-based vectors are M13mp 18 and pUC 19 vectors (Yarnish-Perron et al., Gene 33, 103–119 (1985)), pRK5-based vectors (EP 307,247 published Mar. 15, 1989), pUC118 (Viera and Messing, *Methods Enzymol.* 153:3–11 (1987)), pBluescribe (Stratagene), and pBluescript (Stratagene). Other phagemid vectors may contain the origins of replication of other phages, such as F1. Such vectors usually also contain a pBR322 origins of replication, a drug resistance coding gene, and a polylinker inserted in frame into the portion of the lacZ gene coding for the alpha peptide. (See, e.g. Ausubel et al., Current Protocols in Molecular Biology, John Wiley and Sons, publ. (1991), Unit 1.15.7.) Derivatives of the phage λ that are used as cloning vectors typically contain restriction sites that flank some or all of the dispensable genes in about the middle third of the λ genome. DNA can be inserted and packaged into such phages in vitro. λ phage cloning vectors are well known in the art, and are disclosed, for example, in Ausubel et al., supra, Units 1.10–1.11. Some representative λ vectors include λRK18 (Klein et al., supra); λ Max1 (Clontech); λ EMBL3, λ2001, λgt10, λgt11, Charon 4a, Charon 40, λZAP (e.g. λZAP/R, λZAP/L) the latter most 7 of which are disclosed in Ausubel et al., supra. λ-based vectors allow for efficient cloning of large numbers of cDNAs, and subsequent conversion to a plasmid library (for example in suitable bacterial cells, e.g. *E. coli*) that can be introduced into yeast.

Yeast cells may be transformed with the plasmid library obtained by any technique known in the art. For example, transformation may be performed using lithium acetate (LiAc) in TE buffer, essentially as described in Gietz et al., *Nucl. Acid. Res.* 20(6), 1425 (1992). Alternatively, efficient transformation may be achieved by using the spheroplast transformation procedure, described, for example, in Ausubel et al., supra, Unit 13.7.3. Preferably, transformation is done by electroporation, as described previously. While a *Saccharomyces cerevisiae* strain is preferably employed with the present invention, the practice and scope of this invention should not be construed as being limited exclusively to this species. Any yeast organism which natively lacks the ability to express the reporter gene function, preferably degrade starch (i.e is non-amylolytic), and which is capable of being transformed by the above listed techniques so as to be rendered capable of reporter gene function, preferably starch degradation, is useable with this invention. For example, *Schizosaccharomyces pombe, Hansenula polymorpha, Kluveromyces lactis* and *Pichia pastoris*. Clementi, R. & Rossi, J. (1986) *Antonie van Leeuwenhoek* 52; 343–352.

Alternatively, yeast strains which naturally do contain reporter gene function, for example, those that produce starch degrading enzymes (i.e are amylolytic), can be employed with the present invention, provided that the natural signal sequence for such reporter protein has been inactivated. The inactivation or "knock-out" may be accomplished by any known technique commonly employed in the art, e.g. site-directed mutagenesis. Additional techniques of inactivation are described in Ausubel, Chapter 8, supra. A suitable technique typically employs inactivating the entire gene by removing a large portion of it and replacing the deletion with a selectable marker (e.g. URA3, LEU2, HIS3). This inactive gene-marker fused hybrid can then be used to replace the functional, chromosomal copy of the gene within the cell by homologous recombination following transformation (Rothstein, R. *Methods Enzymol.* 194:281–301 (1991)). Suitable amylolytic yeast strains which can be employed with this technique are described above under the definition of amylase.

After transformation, the yeast colonies are grown on selective media in order to detect the desired transformants by virtue of the secreted reporter gene function. Detection may be effected by any technique commonly employed in the art. For example, in embodiments using amylase fusions, detection can be done by (1) replica plating from the growth medium onto a YEPD-starch medium, (2) growth on a selective medium wherein starch was also incorporated, and (3) growth on a selective medium wherein starch is covalently attached to a readily identifiable dye.

Applicant has discovered that the replica plating step can be preferably deleted by incorporation of the reporter protein substrate, e.g. starch in the case of amylase, directly into the selective growth media. The elimination of the replica plating step saves considerable time and effort, compared for example to colonies selected using invertase where it typically take 7–10 days to grow in the invertase screen following replica plating. The reporter substrate concentration can also be varied in order to adjust the sensitivity of the detection screen. That is, lower substrate concentrations would be expected to detect less "functional" or more weakly secreted signal sequences. Contrarily, increasing the substrate concentrations lowers the sensitivity to eliminate some false positives or "noise" within the detection system. Preferably, in the case of starch, concentrations are varied from 0.5% to 2.0%.

The positive yeast colonies can be detected for reporter secretion by any technique known in the art for detecting that reporter protein. In the case of starch degradation by secreted amylase, yeast can be stained by exposure to iodine vapor, which can be accomplished by inverting the agar plate over iodine crystals for a time sufficient to visibly stain the starch in the plate media, e.g. 2–5 minutes. The iodine will form a blue-black staining complex with the starch present in the media, but not with the amylase break down products. In one embodiment, the reporter substrate is bonded to a visible dye whose color change is readily visible when catalyzed by the reporter protein. Preferably, starch is bound to a visible dye, so that when amylase is secreted by the individual colonies, a clear halo is readily identifiable without further manipulation. Any dye suitable for attachment to starch can be used, as is known in the art. The dye-starch bonding technique and useable dyes preferably employed in the invention are as identified in Biely et al. (*Anal. Biochem.* 172:176–179 (1988)).

Once reporter secreting colonies have been identified, they can be restreaked across fresh selective media (selective for the plasmid marker, e.g. URA3) in order to obtain well defined single colonies. The restreaking process also ensures plasmid maintenance amongst the yeast transformants. In the preferred embodiment, which incorporates the starch directly into the selective media, it has been discovered herein that the time for the restreaking process is diminished vis-a-vis the invertase selection process, e.g. 3 days v. 5–7 days.

The restreaked, transformed colonies can then be analyzed by any technique known in the art to detect novel DNA sequences. For example, the DNA can be isolated and purified, and then compared to known sequences or libraries via hybridization techniques as is known.

Alternatively, and preferably, the DNA present in the yeast colonies can be directly amplified by Polymerase Chain Reaction or PCR. The PCR oligos are designed to start and stop amplification of the reporter vector on either side of the inserted cDNA. The amplified DNA can be readily sequenced or further characterized. The exact primer sequences will vary depending upon the type of reporter yeast expression vector employed. Preferably, the plasmid employed is pSST-amy.1 and the PCR oligos are sequences which anneal to the ADH promotor region and the amylase-encoding gene of the vector as recited in Example 3. However, other suitable amylase expressing vectors and marker annealing PCR oligos will be readily determinable to those of ordinary skill in the art. Amplified DNA sequences are then further isolated and analyzed by known and available techniques, such as column purification, gel electroporation and/or DNA sequencing. The cDNA is compared to known sequences and novelty ascertained. Since known, previously identified signal sequences have been observed to reoccur in the screens or selections described herein, PCR or other DNA characterization methods can be used to rapidly identify positive yeast bearing these known sequences, thus avoiding subsequent isolation and characterization of these frequently occurring non-novel cDNAs.

Novel mammalian secretory leader sequences obtained as described above can be used to screen a second cDNA library. The second cDNA library is constructed in such a way as to contain full-length cDNAs, using known methods and as described above. The second cDNA library, preferably ligated to a mammalian expression vector, is transformed into bacteria, preferably *E. coli*. The library may be screened by hybridization using known screening methods. Alternatively, plasmid DNA is isolated from the transformants for screening by hybridization or using PCR. When screened using PCR, the following general screening protocol may be followed: the cDNA clone containing the novel leader sequence is sequenced, and appropriate oligonucleotide primers are designed. From about one million *E. coli* transformants, pools of about 100,000 transformants are obtained by spreading pools of 10,000 transformants onto 150 mm plates and replicating the pool onto filters. Plasmid DNA is isolated from each pool and PCR is performed using the oligonucleotide primers based on the novel leader sequence. Specific DNA sequences are detected, for example, by gel electrophoresis of the DNA with or without hybridization. Each of the pools is similarly analyzed, and positive pools are subdivided and purified by hybridizing radioactive oligonucleotides directly to the filters as described in Chapter 6 of *Current Protocols in Molecular Biology* and in Chapter 1 of *Molecular Cloning: A Laboratory Manual*.

Using the methods described herein, novel full-length mammalian cDNA clones are isolated. These can be expressed in transient expression systems such as COS cells grown in a culture medium suitable for growth of cells and production of protein. The novel full-length cDNA clones can also be expressed in stable expression systems such as Chinese hamster ovary cells grown in a culture medium suitable for growth of cells and production of protein. In this way the novel secreted and extracellular proteins of the invention encoded by the mammalian cDNAs are produced which may then be assayed for biological activity in a variety of in vitro assays. In addition to detecting novel proteins secreted into the cell culture, the method of the invention also detects and allows isolation of integral membrane proteins, such as receptors, and of proteins which transverse the endoplasmic reticulum to localize in intracellular organelles. The novel secreted proteins produced in accordance with the invention may be purified using known methods. The novel secreted protein thus purified is substantially free of other mammalian proteins.

The method provided herein to detect cDNAs containing signal sequences uses a sensitive assay via a screen to detect the extracellular presence of a reporter. The present method provides the advantage of an increase in sensitivity over the invertase selection, as is apparent in the frequency of positives obtained between the two methods, and the finding that the amylase screen detects a wider range of known secreted proteins. The superiority of the amylase screen over the invertase selection is probably related to either the need for a crucial minimum amount of invertase to be secreted to give a growth phenotype, or the requirement of invertase to oligomerize for full activity; some invertase fusions may result in proteins that are unable to completely oligomerize.

While the initial amylase screening method used libraries derived from liver, a tissue which has a high secretory potential being responsible for secretion of many of the abundant serum proteins, the use of libraries from other tissues resulted in an infidelity in the screen. cDNAs that did not encode typical hydrophobic signal sequences were detected. These sequences, herein termed siren sequences, were also detected with the invertase screen. As demonstrated herein, siren sequences mediate their action via the post-translational secretory pathway in yeast. This conclusion is supported by the observation that allele specific mutations in the Sec71p or Sec72p prevented siren-sequences from scoring in the amylase screen.

It has been suggested that some secreted proteins contain secondary or latent targeting signals which direct the protein into the secretory pathway, although at a much lower efficiencies than observed with a signal sequence. While the present invention is not to be limited by any particular mechanism, it is proposed that amylase contains such signals, which in the signal-sequence-less version of amylase these motifs remain unexposed in the cytoplasm. Addition of a siren sequence causes the destabilization of the amylase protein, which upon unfolding reveals the latent targeting signals. These are subsequently recognized by the post-translational translocation machinery, and the siren sequence-amylase fusion is directed into the secretory pathway. By blocking the post-translational pathway, e.g., by mutants as disclosed herein, the latter steps are prevented from occurring and siren sequences are prevented from scoring in the screen.

Independent of their mechanism of action, the utilization of the loss of halo mutants provides the advantage of a dramatically increased fidelity of the screen. A measure of this is found by analyzing known proteins that are fused to amylase; normally greater than 70% of them encode secreted proteins.

The following examples are offered by way of illustration and not by way of limitation and should not be construed as limiting the invention in any way. The disclosures of all citations in the specification are expressly incorporated herein by reference.

EXAMPLES

Example 1

Construction of Full-length cDNA Library

Isolation of m-RNA

Human fetal liver mRNA was obtained from Clontech Laboratories, Inc. Palo Alto, Calif. USA, catalog no. 64018-1.

The following protocol is described in "Instruction Manual: Superscript® Lamda System for cDNA Synthesis and 1 cloning," cat. No. 19643-014, Life Technologies, Gaithersburg, Md., USA which is herein incorporated by reference. Unless otherwise noted, all reagents were also obtained from Life Technologies. The overall procedure can be summarized into the following steps: (1) First strand synthesis; (2) Second strand synthesis; (3) Adaptor addition; (4) Enzymatic digestion; (5) Gel isolation of cDNA; (6) Ligation into vector; and (7) Transformation.

First Strand Synthesis

Not1 primer-adapter (Life Tech., 2 µl, 0.5 µg/µl) was added to a sterile 1.5 ml microcentrifuge tube to which was added poly A+ mRNA (7 µl, 5 µg). The reaction tube was heated to 70° C. for 5 minutes or time sufficient to denature the secondary structure of the mRNA. The reaction was then chilled on ice and 5×First strand buffer (Life Tech., 4 µl), 0.1 M DTT (2 µl) and 10 mM dNTP Mix (Life Tech., 1 µl) were added and then heated to 37° C. for 2 minutes to equilibrate the temperature. Superscript II® reverse transcriptase (Life Tech., 5 µl) was then added, the reaction tube mixed well and incubated at 37° C. for 1 hour, and terminated by placement on ice. The final concentration of the reactants was the following: 50 mM Tris-HCl (pH 8.3); 75 mM KCl; 3 mM $MgCl_2$; 10 mM DTT; 500 µM each dATP, dCTP, dGTP and dTTP; 50 µg/ml Not 1 primer-adapter; 5 µg (250 mg/µl) mRNA; 50,000 U/ml Superscript II® reverse transcriptase.

Second Strand Synthesis

While on ice, the following reagents were added to the reaction tube from the first strand synthesis, the reaction well mixed and allowed to react at 16° C. for 2 hours, taking care not to allow the temperature to go above 16° C.: distilled water (93 µl); 5×Second strand buffer (30 µl); dNTP mix (3 µl); 10 U/µl E. Coli DNA ligase (1 µl); 10 U/µl E. Coli DNA polymerase I (4 µl); 2 U/µl E. Coli RNase H (1 µl). 10 U T4 DNA Polymerase (2 µl) was added and the reaction continued to incubate at 16° C. for another 5 minutes. The final concentration of the reaction was the following: 25 mM Tris-HCl (pH 7.5); 100 mM KCl; 5 mM $MgCl_2$; 10 mM $(NH_4)_2SO_4$; 0.15 mM β-NAD+; 250 µM each dATP, dCTP, dGTP, dTTP; 1.2 mM DTT; 65 U/ml DNA ligase; 250 U/ml DNA polymerase I; 13 U/ml Rnase H. The reaction has halted by placement on ice and by addition of 0.5 M EDTA (10 µl), then extracted through phenol:chloroform:isoamyl alcohol (25:24:1, 150 µl). The aqueous phase was removed, collected and diluted into 5M NaCl (15 µl) and absolute ethanol (−20° C., 400 µl) and centrifuged for 2 minutes at 14,000×g. The supernatant was carefully removed from the resulting DNA pellet, the pellet resuspended in 70% ethanol (0.5 ml) and centrifuged again for 2 minutes at 14,000×g. The supernatant was again removed and the pellet dried in a speedvac.

Adapter Addition

The following reagents were added to the cDNA pellet from the Second strand synthesis above, and the reaction was gently mixed and incubated at 16° C. for 16 hours: distilled water (25 µl); 5×T4 DNA ligase buffer (10 µl); Sal I adapters (10 µ); T4 DNA ligase (5 µl). The final composition of the reaction was the following: 50 mM Tris-HCl (pH 7.6); 10 mM $MgCl_2$; 1 mM ATP; 5% (w/v) PEG 8000; 1 mM DTT; 200 µg/ml Sal 1 adapters; 100 U/ml T4DNA ligase. The reaction was extracted through phenol:chloroform:isoamyl alcohol (25:24:1, 50 µl), the aqueous phase removed, collected and diluted into 5M NaCl (8 µl) and absolute ethanol (−20 ° C., 250 µl). This was then centrifuged for 20 minutes at 14,000×g, the supernatant removed and the pellet was resuspended in 0.5 ml 70% ethanol, and centrifuged again for 2 minutes at 14,000×g. Subsequently, the supernatant was removed and the resulting pellet dried in a speedvac and carried on into the next procedure.

Enzymatic Digestion

To the cDNA prepared with the Sal 1 adapter from the previous paragraph was added the following reagents and the mixture was incubated at 37° C. for 2hours: DEPC-treated water (41 µl); Not 1 restriction buffer (REACT, Life Tech., 5 µl), Not 1 (4 µl). The final composition of this reaction was the following: 50 mM Tris-HCl (pH 8.0); 10 mM $MgCl_2$; 100 mM MaCl; 1,200 U/ml Not 1.

Gel Isolation of cDNA

The cDNA is size fractionated by acrylamide gel electrophoresis on a 5% acrylamide gel, and any fragments which were larger than 1 Kb, as determined by comparison with a molecular weight marker, were excised from the gel. The cDNA was then electroeluted from the gel into 0.1×TBE buffer (200 µl) and extracted with phenol:chloroform:isoamyl alcohol (25:24:1, 200 µl). The aqueous phase was removed, collected and centrifuged for 20 minutes at 14,000×g. The supernatant was removed from the DNA pellet which was resuspended in 70% ethanol (0.5 ml) and centrifuged again for 2 minutes at 14,000×g. The supernatant was again discarded, the pellet dried in a speedvac and resuspended in distilled water (15 µl).

Ligation of cDNA Into pRK5 Vector

The following reagents were added together and incubated at 16° C. for 16 hours: 5×T4 ligase buffer (3 µl); pRK5, Xho1, Not1 digested vector, 0.5 µg, 1 µl); cDNA prepared from previous paragraph (5 µl) and distilled water (6 µl). Subsequently, additional distilled water (70 µl) and 10 mg/ml tRNA (0.1 µl) were added and the entire reaction was extracted through phenol:chloroform:isoamyl alcohol (25:24:1). The aqueous phase was removed, collected and diluted into SM NaCl (10 µl) and absolute ethanol (−20° C., 250 µl). This was then centrifuged for 20 minutes at 14,000× g, decanted, and the pellet resuspended into 70% ethanol (0.5 ml) and centrifuged again for 2 minutes at 14,000×g. The DNA pellet was then dried in a speedvac and eluted into distilled water (3 µl) for use in the subsequent procedure.

Transformation of Library Ligation Into Bacteria

The ligated cDNA/pRK5 vector DNA prepared previously was chilled on ice to which was added electrocompetent DH10B bacteria (Life Tech., 20 µl). The bacteria vector mixture was then electroporated as per the manufacturers recommendation. Subsequently SOC media (1 ml) was added and the mixture was incubated at 37° C. for 30 minutes. The transformants were then plated onto 20 standard 150 mm LB plates containing ampicillin and incubated for 16 hours (370° C.) to allow the colonies to grow. Positive colonies were then scraped off and the DNA isolated from the bacterial pellet using standard CsCl-gradient protocols. For example, Ausuble et al., 2.3.1.

Example 2

Construction of Enriched 5'-cDNA Library

The following process results in a bias of cDNA fragments which preferentially represents the 5' ends of those cDNA's contained within the previously prepared full length library of Example 1.

Linearize the Full-length Library

10 µg of the pooled isolated full-length library plasmid DNA (41 µl) of Example 1 was combined with Not 1 restriction buffer (New England Biolabs, 5 µl) and Not 1 (New England Biolabs, 4 µl) and incubated at 37° C. for one hour. The reaction was extracted through phenol:chloroform:isoamyl alcohol (25:24:1, 50 µl), the aqueous phase removed, collected and resuspended into 5M NaCl (5 µl) and absolute ethanol (−20° C., 150 µl). This was then centrifuged for 20 minutes at 14,000×g, decanted, resuspended into 70% ethanol (0.5 ml) and centrifuged again for 2 minutes at 14,000×g. The supernatant was then removed, the pellet dried in a speedvac and resuspended in distilled water (10 µl).

Sp6 Transcripts Synthesis

The following protocol was taken from InvitroScript Cap Kit (Invitrogen). The following reagents were brought together and incubated at 37° C. for 2 hours: distilled water (3 µl); linearized DNA library (prepared previously, 1 µg, 1 µl); Ribonucleotide mix (Invitrogen, 10 µl); transcription buffer (Invitrogen, 2 µl) and Sp6 enzyme mix. The reaction was then extracted through phenol:chloroform:isoamyl alcohol (25:24:1, 50 µl) and the aqueous phase was removed, collected and resuspended into 5M NaCl (5 µl) and absolute ethanol (−20° C., 150 µl) and centrifuged for 20 minutes at 14,000×g. The pellet was then decanted and resuspended in 70% ethanol (0.5 ml), centrifuged again for 2 minutes at 14,000×g, decanted, dried in a speedvac and resuspended into distilled water (10 µl).

cDNA Production From Sp6 RNA Overview

The procedure employed was the same as that used to create the full-length cDNA library described in Example 1, except with the following noted differences:

First strand synthesis

6 Nucleotide oligomer random primers were used to prime the first strand cDNA synthesis from the Sp6 RNA transcript in order to create random fragments of cDNA instead of priming from the poly A tail to create a long full-length cDNA.

Adapter ligation

A Sal I adapter (Life Tech.) was alternatively substituted in place of the Not 1 adapter.

Restriction enzyme digestion

Cla 1 or alternatively Sfi 1 were used in place of Not 1. This cuts at a restriction site 5' to the inserted cDNA within the full length library. As a result, only those fragments which correspond to the 5' ends of cDNA present in the full length library were identified.

Gel isolation

Fragments of cDNA corresponding in size to 500–1000 base pairs were isolated. This size range was selected because it is believed that significantly shorter fragments may generate greater numbers of fortuitous and spurious signal sequences during the yeast screen.

First Strand Synthesis

The following reagents were brought together and heated at 70° C. for 5 minutes in order to denature the secondary structure of the mRNA: Sp6 transcript prepared previously (5 µg, 7 µl); N6 primer-adapter (Life Tech., 2 µl). The reaction was halted by placement on ice and First strand buffer (Life Tech., 4 µl), 0.1 M DTT (2 µl) and dNTP mix (1 µl, 10 mM each dNTP) were added and then heated to 37° C. for 2 minutes the temperature. Superscript II® reverse transcriptase (Life Tech., 5 µl) was then added and the reaction incubated at 37° C. for 1 hour, then terminated by placement on ice.

Second Strand Synthesis

While on ice, the following reagents were added to the reaction tube from the first strand synthesis and then reacted at 16° C. for 2 hours: distilled water (93 µl); Second strand buffer (Life Tech., 30 µl); dNTP mix (3 µl); 10 U/µl E. Coli DNA ligase(1 µl); 10 U/µl E. Coli DNA polymerase I (4 µl); 2 U/µl E.coli RNase H (1 µl). 10 U T4 DNA Polymerase (Life Tech.,2 µl) was added and the reaction continued to incubate at 16° C. for another 5 minutes. The reaction was halted by the addition of 0.5 M EDTA (10 µl) and extracted through phenol:chloroform:isoamyl alcohol (25:24: 1). The aqueous phase was removed, collected then diluted into 5M NaCl (15 µl) and absolute ethanol (−20° C., 400 µl) and centrifuged for 20 minutes at 14,000×g. The DNA pellet was then decanted and resuspended in 70% ethanol (0.5 ml) and centrifuged again for 2 minutes at 14,000×g. The supernatant was then removed and the pellet dried in a speedvac.

Adapter Addition

The following reagents were added to the DNA pellet obtained from the Second strand synthesis and reaction was incubated for 16 hours at 16° C.: distilled water (25 µl);

5×T4 DNA ligase buffer (Life Tech., 10 μl); Sal 1 adapters (10 1μl); T4 DNA ligase (5 μl). The reaction was extracted though phenol:chloroform:isoamyl alcohol (25:24:1, 50 μl) and the aqueous phase was removed, collected and diluted into 5M NaCl (8 μl) and absolute ethanol (−20° C., 250 μl), then centrifuged for 20 minutes at 14,000×g. The DNA pellet was decanted and suspended into 70% ethanol (0.5 ml) and centrifuged again for 2 minutes at 14,000×g. The supernatant was removed and the residue pellet dried in a speedvac.

Enzymatic Digestion

The following reagents were added to the DNA pellet obtained from the adapter addition reaction and the reaction was incubated at 37 ° C. for one hour: distilled water (41 μl); Cla 1 restriction buffer (New England Biolabs, 5 μl) and Cla 1 (New England Biolabs, 4 μl).

Gel Isolation of DNA

The digested DNA from the digestion procedure above was size fractionated by acrylamide gel electrophoresis on a 5% acrylamide gel. cDNA fragments greater than 500–1000 base pairs in size, as determined by comparison with known molecular weight markers, were excised from the gel. The cDNA was electroeluted from the acrylamide gel into 200 μl of 0.1×TBE buffer and extracted with phenol:chloroform:isoamyl alcohol (25:24:1, 200 μl). The aqueous phase was removed, collected and diluted by 5M NaCl (20 μl) and absolute ethanol (−20° C., 600 μl). This was centrifuged for 20 minutes at 14,000×g, decanted, resuspended in 70% ethanol (0.5 ml) and centrifuged again for 2 minutes at 14,000×g. The supernatant was removed, the pellet dried in a speedvac and resuspended into distilled water (15 μl).

Ligation Into pSST-amy.1 Vector

The following reagents were added together and incubated at 16° C. for 16 hours: 5×T4 ligase buffer (Life Tech., 3 μl); pRK5 Cla-Sal digested vector, 0.5 μl, 1 μl); cDNA prepared from the digestion (5 μl); distilled water (6 μl). Subsequently, additional distilled water (70 μl) and 10 mg/ml tRNA (0.1 μl) was added and the entire reaction was extracted through phenol:chloroform:isoamyl alcohol (25:24: 1, 100 μl). The aqueous phase was removed, collected and diluted by 5M NaCl (10 μl) and absolute ethanol (−20° C., 250 μl) and centrifuged for 20 minutes at 14,000×g. The DNA pellet was decanted, resuspended into 70% ethanol (0.5 ml) and centrifuged again for 2 minutes at 14,000×g. The supernatant was removed and the residue pellet was dried in a speedvac and resuspended in distilled water (3 μl).

Transformation

The ligated cDNA/pSST-amy.1 vector DNA prepared previously was chilled on ice to which was added electrocompetent DH10B bacteria (Life Tech., 20 μl). The bacteria vector mixture was then electroporated as recommended by the manufacturer. Subsequently, SOC media (Life Tech., 1 μl) was added and the mixture was incubated at 37° C. for 30 minutes. The transformants were then plated onto 20 standard 150 mm LB plates containing ampicillin and incubated for 16 hours (370° C.). Positive colonies were scraped off the plates and the DNA was isolated from the bacterial pellet using standard protocols, e.g. CsCl-gradient, Ausubel, Unit 2.3. The purified DNA was then carried on to the yeast protocols of Example 3.

Example 3

Screening For Secretion Positive Yeast

The yeast methods employed in the present invention were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

While any yeast strain containing a stable mutant ura3 is useable with the present invention, the preferable yeast strain used with the practice of the invention was HD56-5A (ATCC-90785). This strain had the following genotype: MAT alpha, ura3-52, leu2-3, leu2-112, his3-11, his3-15, MAL$^+$, SUC$^+$, GAL$^+$. Because this strain was MAL$^+$, that is, it could use maltose as a sole carbon energy source, amylase was tested for whether it could be used as a selectable marker. However, we found insufficient secretion of amylase in combination with maltose activity to support colony growth in the absence of glucose. Instead, the detection of amylase secretion alone became the selection criteria.

Transformation

Transformation was performed based on the protocol outlined by Gietz, D. et al., *Nucl. Acid. Res.* 20, 1425 (1992). With this procedure, we obtained transformation efficiencies of approximately 1×10$^5$ transformants per microgram of DNA. Transformed cells were then inoculated from agar into YEPD complex media broth (100 ml) and grown overnight at 30° C. The YEPD broth was prepared as described in Kaiser et al., *Methods in Yeast Genetics*, Cold Spring Harbor Press, Cold Spring Harbor, N.Y., USA, p. 207 (1994). The overnight culture was then diluted to about 2×10$^6$ cells/ml (approx. OD$_{600}$=0.1) into fresh YEPD broth (500 ml) and regrown to 1×10$^7$ cells/ml (approx. OD$_{600}$= 0.4–0.5). This usually took about 3 hours to complete.

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM Li$_2$OOCCH$_3$), and resuspended into LiAc/TE (2.5 ml).

Transformation took place by mixing the prepared cells (100 μl) with freshly denatured single stranded salmon testes DNA (Lofstrand Labs, Gaithersburg, Md., USA) and transforming DNA (1 μg, vol.<10 μl) in microfuge tubes. The mixture was mixed briefly by vortexing, then 40% PEG/TE (600 μl, 40% polyethylene glycol-4000, 10 mM Tris-HC, 1 mM EDTA, 100 mM Li$_2$OOCCH$_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5–10 seconds, decanted and resuspended into TE (500 μl, 10 mM Tris-HCl, 1 mM EDTA pH 7.5) followed by recentrifugation. The cells were then diluted into TE (1 ml) and aliquots (200 μl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics*, Cold Spring Harbor Press, Cold Spring Harbor, N.Y., USA, p. 208–210) (1994). Transformants were grown at 30° C. for 2–3 days.

Detection of Clones Containing Secreted Proteins

The detection of colonies secreting amylase was performed by any of the several methods: (1) Replica plating onto YEPD-starch agar; (2) Selective media growth including starch; (3) Selective media growth including red starch. The invention is preferably practiced by the latter of the following three described techniques.

Replica Plating

After growth on the SCD-Ura agar was complete, the transformants were transferred by replica plating onto YEPD agar containing 2.0% (w/v) soluble potato starch (Sigma). Following the replica plating step, the colonies were allowed to regrow at 30° C. for 24–48 hours. Colonies in which amylase was secreted by signal sequences were detected by inverting the agar plate containing the colonies over exposed iodine crystals for 2–5 minutes. The iodine formed a blue-black staining complex with the starch present in the media, but not with the amylase break down products. The amylase secreting colonies, and ergo secreted proteins or signal sequence containing cDNA's were identified by a distinct halo of non-stained agar around the positive colony.

Starch concentrations in the YEPD agar was varied between 2.0% and 0.5% (w/v) and it was discovered that these starch concentrations could differentiate cells secreting amylase from those not secreting amylase.

Selective Media Growth Including Starch

Starch was also directly incorporated into the SCD-Ura agar at concentrations of 2.0%, 1.0% and 0.5% (w/v) and it was discovered that amylase secreting positives were detected provided that the media was buffered to a final pH of 7.0 with a potassium phosphate buffering system (final concentration 50 or 100 mM). This effectively eliminated the replica plating step. Buffering was necessary because the optimumpH for the mouse pancreatic amylase used in this example was 7.0 and the yeast media often is or becomes acidic due to the fermentation of glucose by the yeast.

Selective Media Growth Including Red Starch

Starch was coupled to the red dye (Reactive Red-120, Sigma) as per the procedure described by Biely et al, *Anal. Biochem.* 172, 176–179 (1988). The coupled starch was incorporated into the SCD-Ura agar plates at a final concentration of 0.15% (w/v), and was buffered with potassium phosphate to a pH of 7.0 (50–100 mM final concentration). The use of the red starch eliminated both the replica plating step as well as the need to perform any staining—the positive colonies were readily distinguishable without any further manipulation.

The positive colonies from any of the above three detection methods were picked and streaked across fresh selective media (onto 150 mm plates) in order to obtain well isolated and identifiable single colonies. This step also ensured maintenance of the plasmid amongst the transformants. Well isolated single colonies positive for amylase secretion were detected either by replica plating onto YEPD/Starch agar, or by direct incorporation of starch or red starch into buffered SCD-Ura agar. Positive colonies were determined by their ability to break down starch resulting in a clear halo around the positive colony visualized either directly (red starch) or following iodine staining of the starch.

Isolation of DNA by PCR Amplification

When a positive colony was isolated, a portion of it was picked by a toothpick and diluted into sterile water (30 µl) in a 96 well plate. At this time, the positive colonies were either frozen and stored for subsequent analysis or immediately amplified. An aliquot of cells (5 µl) was used as a template for the PCR reaction in a 25 µl volume containing: 0.5 µl Klentaq (Clontech, Palo Alto, Calif.); 4.0 µl 10 mM dNTP's (Perkin Elmer-Cetus); 2.5 µl Kentaq buffer (Clontech); 0.25 µl forward oligo 1; 0. µl reverse oligo 2; 12.5 µl distilled water. The sequence of the forward oligonucleotide 1 was:

5'-TGTAAAACGACGGCCAGT
TAAATAGACCTGCAATTATTAATCT-3'    [SEQ ID NO: 2]

The sequence of reverse oligonucleotide 2 was:

5'-CAGGAAACAGCTATGACC
ACCTGCACACCTGCAAATCCATT-3'    [SEQ ID NO: 3]

PCR was then performed as follows:

| a. | | Denature | 92° C., 5 minutes |
|---|---|---|---|
| b. | 3 cycles of | Denature | 92° C., 30 seconds |
| | | Anneal | 59° C., 30 seconds |
| | | Extend | 72° C., 60 seconds |
| c. | 3 cycles of | Denature | 92° C., 30 seconds |
| | | Anneal | 57° C., 30 seconds |
| | | Extend | 72° C., 60 seconds |
| d. | 25 cycles of | Denature | 92° C., 30 seconds |
| | | Anneal | 55° C., 30 seconds |
| | | Extend | 72° C., 60 seconds |
| e. | | Hold | 4° C. |

The underlined regions of the oligonucleotides annealed to the ADH promoter region and the amylase region, respectively, and amplified a 307 bp region from vector pSST-AMY1 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused CDNA resulted in considerably longer nucleotide sequences.

Following the PCR, an aliquot of the reaction (5 µl) was examined by agarose gel electrophoresis in a 1% agarose using a Tris-Borate-EDTA (TBE) buffering system as described by Sambrook, J. et al., "Molecular Cloning- A Laboratory Manual" second edition, Cold Spring Harbor Laboratory Press, Cold Spring Harbor, N.Y., USA. Clones resulting in a single strong PCR product larger than 400 bp were further analyzed by DNA sequencing after purification with a 96 Qiaquick PCR clean-up column (Qiagen Inc., Chatsworth, Calif., USA).

Using the procedures outlines in Examples 1–3 CDNA signal sequences were isolated and identified by known DNA sequencing. The identities and frequency of occurrence of each sequence is reported in Table 1 (identified isolated protein from amylase screen of Examples 1–3):

TABLE 1

| PROTEIN | Accession # | No. of Isolates | Frequency (%) |
|---|---|---|---|
| albumin | V00494 | 75 | 33.1 |
| fibrinogen beta | M64983 | 62 | 27.4 |
| novel sequences | — | 38 | 16.8 |
| a-fetoprotein | Z19532 | 12 | 5.3 |
| traG (*E. Coli*) | M59763 | 6 | 2.6 |
| vit. D binding protein | M12654 | 4 | 1.7 |
| heparin perenchall growth f. | D14446 | 3 | 1.3 |
| archain | X81197 | 3 | 1.3 |
| fibrinogen alpha | J00127 | 2 | 0.8 |
| fibrinogen rel. protein | — | 2 | 0.8 |
| heparin cofactor II | M12849 | 1 | 0.4 |
| kininogen | K02566 | 1 | 0.4 |
| fibrinogen gamma | X02415 | 1 | 0.4 |
| compl. factor h-like | M65293 | 1 | 0.4 |
| a-1 antitrypsin | X01683 | 1 | 0.4 |
| aminopeptidase A | L12468 | 1 | 0.4 |
| HGF activator-like | D49742 | 1 | 0.4 |
| b-2-glycoprotein | X57847 | 1 | 0.4 |
| uracil DNA glycoprotein | X15653 | 1 | 0.4 |

TABLE 1-continued

| PROTEIN | Accession # | No. of Isolates | Frequency (%) |
|---|---|---|---|
| eryth. 50 kD glycoprotein | X64594 | 1 | 0.4 |
| fragile X homolog | U25165 | 1 | 0.4 |
| glycophorin A | X08054 | | |
| neurotensin N | S47339 | 1 | 0.4 |
| C-reactive protein | X56214 | 1 | 0.4 |
| adrenomedullin | D14874 | 1 | 0.4 |
| inter-a-trypsin inhibitor | X07173 | 1 | 0.4 |
| mitochondrial COX-1 | M12548 | 1 | 0.4 |
| GST1 GTP binding protein | X17644 | 1 | 0.4 |
| ribosomal protein s23 | D14530 | 1 | 0.4 |

Example 4

Invertase Selection For Secretion Positive Yeast

Using the procedure published in Klein et al. describing the invertase selection process, signal sequences were detected, subject to DNA sequencing, and their identities and frequency of occurrence are reported in Table 2.

TABLE 2

Identified protein from invertase selection of Example 4

| PROTEIN | Number of Isolates | Frequency (%) |
|---|---|---|
| albumin | 76 | 50.6 |
| b-2-glycoprotein | 27 | 18.0 |
| fibrinogen beta | 14 | 9.3 |
| novel | 8 | 5.3 |
| kininogen | 8 | 5.3 |
| afamin | 2 | 1.3 |
| M130 antigen | 2 | 1.3 |
| heparin parench. growth f. | 2 | 1.3 |
| heparin cofactor ii | 2 | 1.3 |
| hemopexin | 1 | 0.6 |
| complement factor I | 1 | 0.6 |
| a-1 anti-trypsin | 1 | 0.6 |
| apolipoprotein B1 | 1 | 0.6 |
| a-2-hs-glycoprotein | 1 | 0.6 |
| fibrinogen gamma | 1 | 0.6 |
| a-fetoprotein | 1 | 0.6 |
| tumor protein p21 | 1 | 0.6 |
| ribosomal protein s15 | 1 | 0.6 |

In comparing Tables 1 & 2, it will be noted that the amylase screen identified 315 positives from $1.6 \times 10^6$ Ura$^+$ colonies, or a frequency of 1 in 5000. Among these, it was possible to sequence and identify 226 of these clones. In the invertase selection process, 272 Suc$^+$ positives were identified from $8 \times 10^6$ Ura$^+$ colonies, or a frequency of 1 in 29,000. From the invertase selection assay, it was possible to sequence 150 clones.

As a result, it is clear that the amylase screen as practiced above resulted in a system which is about 6-fold more sensitive than the invertase. Moreover, this increased sensitivity occurred with about 4 fold fewer organisms screened. By including starch in the medium that selects for the gain of plasmid, the transformants are screened directly for the presence of a signal sequence in one step. The amylase process has eliminated the need for a replica plating step. Once the preliminary transformations have been performed, the positives can be directly identified; there is no need to either replica plate the transformants or to scrape and pool them prior to retesting for the invertase phenotype. This represents a considerable reduction in the time and resources necessary to complete the signal sequence analysis. In contrast, protocols using invertase require further testing to identify the signal sequence containing clones after transformation. The present method eliminates much of the labor required by the invertase procedure (e.g., replica plating or pool and re-plating). Furthermore, as is indicated on FIG. 2, while the prior art screening method can take up to 21 days, the present invention may be completed in as few as 6 days. This translates to over a 3 fold decrease in time of completion of the screening procedure.

Moreover, a comparison of Tables 1 and 2 indicates a larger diversity of proteins identified with amylase than with invertase. This ultimately results in 16% of the sequences obtained from the amylase screen being novel rather than the 5% obtained with invertase.

The amylase system is more robust, providing positives with a wider variety of secreted proteins than does the invertase system. The proportion of known secreted proteins able to function in the amylase screen compared to the invertase selection was determined. A "library" of ten known secreted proteins was used to define which signal sequences function with these reporters in a simulated screening situation. A "library" of known secreted proteins was constructed using the same protocol as described herein (5' ends were subcloned using an SP6 transcript and random priming protocol and ligated into the pSST-INV or pSST-AMY vectors) with a mixture of the following cDNAs in pRK5 as starting material: leptin receptor (GenBank accession U43168); DNase I (M55983); DNase homolog DNA-SIL2 (U62647); alkaline phosphatase (M13077); interleukin-12 (U03187); TPO receptor (M90103); interleukin 6 (M29150); acid-labile subunit of IGF binding protein (M86826); BMP-3 (M22491); and thrombopoetin (L34169). With the invertase system it was found herein that only one of these proteins, leptin receptor was capable of giving positive clones. Using the same ten proteins, 5 proteins are capable of directing amylase into the medium, namely, leptin receptor, thrombopoeitin receptor, interleukin-6, alkaline phosphatase and thrombopoeitin.

Example 5

Siren Sequences

In the process of analyzing the mammalian cDNA sequences yielding positive fusions in the amylase and invertase systems, at least two classes of sequences were found that mimicked authentic signal peptides. These signal sequence peptide mimics derived from non-secreted mammalian protein sequences and from either the 5' or 3' untranslated sequences that flank mammalian cDNA coding sequences. In some cases these sequences were structurally similar to authentic signal peptides. Surprisingly, one family of sequences was observed that did not contain authentic signal sequences, and was not structurally similar to authentic signal sequences, lacking hydrophobic stretches that could act as an ectopic signal sequence when fused to amylase. These initially alluring but non-authentic signal sequences are termed "siren sequences," reminiscent of the alluring mythical creatures that led mariners off course.

Noticeable among the siren sequences are sequences derived from non-secreted proteins such as ribosomal subunits (e.g., RS20_HUMAN), transcription factors (e.g., BTF3_HUMAN), nucleosomal factors, elongation factors (e.g., EF11_HUMAN), RNA helicase (e.g., P68_HUMAN), ribonucleoproteins (e.g., ROA_HUMAN). These siren sequences were found useful to determine conditions or discover genetic mutations in yeast that selectively prevented or reduced secretion of fusions containing N-terminal siren sequences.

Siren sequences were most evident when libraries derived from tissues other than liver were screened. The fidelity of the screen was compromised as judged by the percentage of known not secreted proteins appearing in the screens. These screens also contained very high proportions of novel sequences. Presumably this is, in part, because other tissues do not have such a high proportion of their mRNAs devoted to secreted proteins as liver. Since the human genome contains approximately 20% random sequences that are capable of coding for a functional signal sequence in yeast when supplied with a initiator ATG codon, an infrequent occurrence of sequences derived from non-coding regions or alternate reading frames contaminating our positive clones was expected. The relatively high frequency of siren sequences was unexpected. The direct consequence of the short hydrophobic random sequences from UTRs and the non-hydrophobic siren sequences is that the signal to noise ratio is dramatically decreased and the screen detected significant numbers of clones without true signal sequences.

Example 6

Avoiding Siren Sequences—Isolation of Loss of Halo Mutants

Since the siren sequences led to isolating unwanted cDNAs that encoded non-secreted proteins, an attempt was made to eliminate or reduce such sequences from scoring positive in an assay, thereby increasing the signal to noise ratio in the assay. Taking advantage of the power of yeast genetic techniques and the ability to manipulate readily the yeast genome, a method was devised to isolate yeast mutants that were unable to score siren-amylase fusions as positive in the screen.

First, a siren-amylase fusion plasmid was constructed. DNA encoding a siren sequence from the protein subunit of the non-secreted human 40S ribosome particle (RPS20; Swiss Protein accession number RS20_HUMAN) was ligated 5' to DNA encoding murine amylase that was lacking a signal peptide (SEQ ID NO: 1). The resultant fusion protein (RS20-AMY; SEQ ID NO: 4; FIG. 4) does not contain any notable regions of hydrophobicity that could act as a signal sequence, as analyzed by hydropathy calculations as shown in FIG. 5. This construct was used to screen for mutant cells unable to produce a halo (positive score) when transformed with this plasmid, as follows.

Haploid yeast cells (strain W303 either MATα or MATa) were mutagenized by either chemical mutagenesis with ethylmethansulfonate (EMS) or by exposure to UV irradiation to 30–50% percent survival, as previously described (Sherman et al., *Methods in yeast genetics; a laboratory course manual*. Cold Spring Harbor Laboratory Press, N.Y., (1986)). Following mutagenesis the cells were allowed to recover for a period of 4–8 hours prior to harvesting and transformation with the reporter plasmid (Gietz et al., *Improved method for high efficiency transformation of intact yeast cells. Nucleic Acids Res.* 20:1425 (1992)). Plasmid-bearing transformants were selected on synthetic complete lacking uracil ("SC-Ura") medium containing 0.15% red starch, as previously described in Example 3.

Loss of halo mutants that produced no halo or a reduced sized halo were picked and further characterized.

Example 7

Avoiding Siren Sequences—Phenotypic Characterization of Loss of Halo Mutants

The loss of halo mutants were analyzed in two ways. In one approach the loss of halo mutants were mated to an isogenic yeast strain to form a diploid that also contained the reporter plasmid. The diploids were scored for their halo phenotype. A diploid that possessed a similar halo phenotype to a wild-type diploid were considered to have a recessive loss of halo mutant parent. Diploids that had a reduced halo phenotype compared to wild-type controls were considered to have a dominant loss of halo mutant parent. Only recessive mutants were further analyzed.

For the recessive mutants it was determined whether the mutagenic event was the result of a mutation within the yeast chromosome or from a mutation within the protein coding region of the reporter plasmid. This was accomplished using a plasmid "curing" technique in which cells which had lost the reporter plasmid were selected for the ura⁻ (ura minus) phenotype on 5 Fluoro-orotic acid media (Boeke et al., *A positive selection for mutants lacking orotidine-5'-phosphate decarboxylase activity in yeast: 5-Fluoro-orotic acid. Molecular and General Genetics* 197:345–346. 1984)). Subsequently, the plasmid-less cells were retransformed with fresh aliquots of reporter plasmid. Strains which still exhibited a mutant phenotype after curing and retransformation were considered to contain chromosomal mutations that were responsible for the loss of halo phenotype. Strains which lost the loss of halo phenotype upon curing and retransformation were considered to originally have possessed plasmid-linked mutations and were not considered for further analysis. Only chromosomal-linked, recessive mutants were further characterized.

Mutants were expected to be of two different classes, namely those which were specific for the loss of halo with only the RS20-AMY fusion, and those which pleiotropically lost the ability of other types of Siren-Amylase sequences to be recognized in the screen.

In order to determine the specificity (or pleiotropy) of the secretion defect phenotype, the recessive mutant strains were independently transformed with a second Siren-Amylase reporter plasmid, which we termed RL15-AMY. This fusion contains an unrelated, non-hydrophobic sequence that also scored positive in the signal screen assay. The sequence was derived from the 3' untranslated region of a cDNA encoding a ribosomal subunit (RL15_HUMAN). The RL15-AMY fusion protein sequence (SEQ ID NO: 5) is shown in FIG. 6. At least six mutants had a pleiotropic loss of halo phenotype when the second Siren-Amylase reporter vector was transformed into them (Table 3).

TABLE 3

Halo Phenotypes Associated With Pleiotropic Loss of Halo Mutants

| | Halo Size When Transformed With: | | |
|---|---|---|---|
| Mutant | pRS20 | pRL15 | pPERT-AMY |
| HWY9 | – | – | + |
| HWY30 | – | – | + |
| HWY4 | – | – | + |
| HWY5 | – | – | + |
| HWY6 | – | – | + |
| DQY140 | – | – | +/– |
| Wild-type | ++++ | ++ | ++ |

Legend

Colonies were scored for halo size, which is an indication of secretory ability. The "–" denotes no observable halo.

Importantly, these mutants still scored positive for a known secreted protein (id peroxidase precursor; PERT_HUMAN) fused to amylase (PERT-AMY; SEQ ID NO: 6, FIG. 8). However the strength of this positive signal, as judged by halo size produced by the mutant, was weaker than the signal from the corresponding construct in wild-type cells (Table 3). The PERT-signal sequence utilizes both the co-translational and post-translational translocation pathways; the decrease in its signal intensity is a result of the loss of transport through the post-translational pathway. Additionally, comparing wild-type to any one of the mutant strains reveals that reduction of RS20 fusion secretion (from "++++" to "−") relative to PERT fusion secretion ("++" to "+" or +/−") was greater. Consequently, these results demonstrate that the loss of halo mutants are not simply affecting the overall sensitivity of the assay, rather they have specifically lost the ability to detect Siren sequences compared to authentic signal sequences in the screening process.

The mutational event resulting in the recessive loss of halo phenotype was due to one genetic locus (or two very closely linked loci), since the loss of halo phenotype segregated with a 2:2 mutant:wild-type pattern during meiosis in all cases examined (Sherman et al., *Methods in yeast genetics; a laboratory course manual*. Cold Spring Harbor Laboratory Press, N.Y., (1986)).

Example 8

Avoiding Siren Sequences—Mapping the Loss of Halo Mutations

To identify the cellular components that were mutated in the loss of halo mutants, in order the define the pathway the Siren-AMY sequences were using to score in the assay, complementation analysis was done using known secretory pathway wild-type SEC genes. Initially, a collection of yeast wild-type SEC genes, which had previously been identified as being involved in the transport of proteins out of the cytoplasm and across the endoplasmic reticulum membrane, was used to transform the mutant strains bearing the RS20-AMY reporter plasmid. Because the mutants were recessive, the corresponding wild-type gene will complement the mutant gene, resulting in a wild-type phenotype and a production of halo. The mutants were transformed with any one of the genes SEC61, SEC62, SEC63, SEC71, SEC72, SSH1, SEB1, SBH1, and SEB2.

The SEC71 and SEC72 genes when present in either multicopy (YEp type) or low copy (YCp type) vectors were able to complement the recessive loss of halo mutants. The complementation results are summarized in Table 4.

AMY reporter. Complementation was again scored by the appearance of halos. Complementing plasmid were purified, retested and analyzed by restriction mapping. Seventeen independently isolated complementing plasmids all showed identity to SEC71 by restriction mapping, consistent with the complementation analysis shown in Table 4.

To further confirm that the mutation mapped to sec71in mutant DQY140, allele rescue (Rothstein, "Targeting, disruption, replacement, and allele rescue: Integrative DNA transformation in yeast," In: Guthrie, C. and Fink, G. R. (Eds.), *Guide to yeast genetics and molecular biology*, Academic Press, San Diego, pp281–301 (1991)) of the sec71allele present in the strain's genome was performed, followed by sequencing the isolated gene. Compared to the wild-type SEC71 sequence (SEQ ID NO: 7), the sec71allele sequence (SEQ ID NO: 8) contains a frameshift that results in a truncated version of the sec71 protein (see FIG. 10).

Sec71p and Sec72p are components of a protein complex, which together with the Sec62p and Sec63p gene products, known as the Sec62-Sec63p complex. The Sec62-Sec63p protein complex functions in post-translation translocation. While not to be limited by any one theory, the present discovery of the loss of halo mutant genotype is consistent with the notion that the post-translational translocation pathway is being utilized for the transport of Siren-AMY fusion proteins, presumably out of the cytoplasm and into the secretory pathway.

Example 9

SEC71 Knockout Phenotype

To further demonstrate that the post-translational translocation pathway is indeed the route being used by the Siren-AMY fusions, we constructed a sec71::LEU2 disruption allele, in which the SEC71 gene has been deleted and replaced with a selectable marker (Rothstein, "Targeting, disruption, replacement, and allele rescue: Integrative DNA transformation in yeast," In: Guthrie, C. and Fink, G. R. (Eds.), *Guide to yeast genetics and molecular biology*, Academic Press, San Diego, pp281–301 (1991)). Such strains are viable, but exhibit a selective defect in post-translational translocation across the ER membrane (Green et al., "Mutants in three novel complementation groups inhibit membrane protein insertion initiation and soluble protein translocation across the endoplasmic reticulum membrane of Saccharomyces cerevisiae," *J. Cell Biol.* 116:597–604 (1992); Fang and Green, "Nonlethal sec71-1

TABLE 4

Complementation Analysis of Loss of Halo Mutants

| Mutant | SEC61 | SEC62 | SEC63 | SEC71 | SEC72 | SSH1 | SSS1 | SEB1 |
|---|---|---|---|---|---|---|---|---|
| HWY9a | − | − | − | − | + | − | − | − |
| HWY30a | − | − | − | + | − | − | − | − |
| HWY4a | − | − | − | + | − | − | − | − |
| HWY5a | − | − | − | + | − | − | − | − |
| HWY6a | − | − | − | + | − | − | − | − |
| DQY140 | − | − | − | + | − | − | − | − |

Legend

+ denotes wild-type phenotype; − denotes mutant phenotype. Consequently, a sec72 mutation is present in HWY9 mutant and a sec71mutation is present in HWY30, HWY4, HWY5, HWY6, and DQY140.

In addition, a library of yeast chromosomal fragments was used to transform the DQY140 mutant bearing the RS20- and sec72-1 mutations eliminate proteins associated with the Sec63p-BiP complex from S. cerevisiae," *Mol. Biol. Cell.* 5:933–942 (1994)). Strains which contained the sec71::LEU2 allele exhibited a loss of halo phenotype when transformed with both types of Siren-AMY fusions. The sec71 knockout strains were observed to secrete a known secreted protein but at a much lower level than wild-type or than the above described mutant strains containing sec71 and sec72 mutations (data not shown).

Example 10

Signal Sequence Screening With sec Mutants

The sec71 mutant DQY205-3 (this strain is a backcrossed derivative of the original mutant DQY140) was used in a screen using libraries that had previously been screened using wild-type cells. Use of this particular sec71 mutant reduced, but did not abolish, transport of siren-amy fusions. A dramatic increase in the fidelity of the screen was achieved, as judged by the percentage of positives containing authentic signal sequences from known secreted proteins compared to non-authentic signal sequences (i.e. siren sequences) from known non-secreted proteins (Table 5). Interestingly, while the percentage of known non-secreted proteins decreased by about two-fold, the percentage of known authentic secreted proteins increased 5- to 10-fold, suggesting an increased efficiency of authentic signal peptide utilization in the sec71 background.

TABLE 5

Comparison of Signal Sequence Screens Performed in Wild-type and sec71 Mutant DQY205-3

| Library | Retina | | Small Intestine | |
|---|---|---|---|---|
| Strain | sec71$^-$ | SEC71$^+$ | sec71$^-$ | SEC71$^+$ |
| Known Secreted | 50 | 5 | 55 | 11 |
| Known Non-Secreted | 10 | 22 | 5 | 9 |
| Novel | 16 | 38 | 27 | 56 |

Legend

Remaining clones consist of known mitochondrial sequences (which contain amino terminal export signals) and known GenBank matches comprising 3' and 5' untranslated regions.

The dramatic decrease of "novels" from the screen, together with the increased screen fidelity, suggests that many of the novel sequences obtained using the wild-type strain were in fact Siren-AMY fusions, i.e. without an authentic signal sequence.

Using the sec71 mutant, known secreted proteins accounted for typically greater than 70%, often greater than 80 to 90%, of the known sequences, providing much superior fidelity when compared to screens using wild-type yeast. Consequently, in the method of the present invention, a significantly higher percentage of the novels will be derived from authentic secreted proteins. Most of the open reading frames (ORF) fused to amylase contained a stretch of hydrophobic residues preceded by an ATG codon and therefore resemble signal sequences. Thus, while known not-secreted proteins were still being identified in this screen, these typically represented a fusion of a spurious ATG-initiated signal sequence in an alternate ORF fused to amylase, rather than a fusion of a known non-secreted protein sequence to amylase.

Depending upon the specific library screened, between 10–30% of the clones were novel, since they do not match proteins or cDNA clones deposited in numerous databases (excluding dbEST). Such clones could represent fusions of novel secreted or membrane proteins to amylase or could represent the spurious hydrophobic ORFs discussed above. To differentiate between these possibilities, the size distribution of ORFs from known secreted protein fused to amylase was analyzed. It was found that the length of known secreted proteins has a relatively sharp cut-off; very few sequences are smaller than 70 residues in length and most are in >100 residues in length. When the novel sequences were analyzed, most of the potential translation products fused to amylase were relatively short (less than 50 residues). Upon applying a similar "size-filter" onto the novel sequences, sequences derived from spurious sequences that mimic signal sequences were eliminated. Further analysis (eg, computer analysis to extend the sequences with overlapping expressed sequence tags or cloning a full-length cDNA) revealed that most long ORFs are derived from novel secreted proteins. Using these criteria, approximately 2% of the clones picked appear to be derived from truly novel proteins. Furthermore, most classes of secreted molecules—soluble molecules, type I and type II membrane proteins as well as multispanning membrane proteins—were identified. Many of the novel proteins have homology to known secreted proteins of known function, suggesting potential roles for the function of these molecules, but many of the clones found represented truly novel molecules having no homology to proteins present in current databases.

In sum, the present invention provides novel sequences with long open reading frames (>50 amino acids) fused to amylase. Such long signal-containing ORFs are preferred sequences that are more likely to be indicative of a true secreted protein. These account for 2–4% of the total sequences found using the sec mutants.

Example 11

Loss of Halo Mutants Are Specific Mutants in the Post-Translational Translocation Pathway To isolate additional mutants that might improve signal sequence screening, mutants defective in post-translational translocation were selected by the method of Ng et al. (*J. Cell Biol.* 134:269–278). In this selection, the signal sequence for carboxypeptidase Y (CPY) was attached to the N-terminus of a cytoplasmic protein encoded by URA3, which is needed for growth of ura3$^-$ cells on uracil-deficient medium. The carboxypeptidase Y signal sequence is reported as one exclusively recognized by the post-translocational secretion pathway. Cells competent for this pathway will secrete CPY-URA3 fusion and not grow on selective medium. Cells that retain the fusion in the cytoplasm will grow. After mutagenesis of the yeast cells, URA$^+$ cells were selected. Forty-one recessive mutants were obtained. These mutants were characterized by complementation with a YEplac vector containing one of SEC61, SEC62, SEC63, SEC71, SEC72, SEB1, SEB2, SSH1, or SSS1. Three strains were complemented by SEC62, three by SEC71, and two by SEC72. Analysis of the remaining strains is on-going.

Each of the genotyped strains were characterized with respect to transport specificity using the RS20-AMY, RL15-AMY and PERT-AMY fusion vectors, scoring for loss of halo phenotype as described above. The results are shown in Table 6.

TABLE 6

Phenotypes of the Mutants with Respect to Transport Specificity Transformed with Reporter Plasmid

| Mutant | pRS20-AMY | pRL15-AMY | pPERT-AMY |
|---|---|---|---|
| sec62-25 | + | − | + |
| sec62-28 | + | ± | ± |
| sec62-34 | + | − | ± |
| sec71-4 | − | − | + |
| sec71-11 | ± | − | ± |
| sec71-16 | − | − | + |
| sec72-39 | ++ | − | + |
| sec72-43 | − | − | + |
| Wildtype | +++ | + | ++ |

Legend

Colonies were scored for halo size, which is an indication of secretory ability. The "−" denotes no observable halo.

As can be seen, mutants defective in the transport of a specific post-translational translocation pathway signal sequence (ssCPY) may in some cases retain the ability to transport some siren-amy fusions as well as proteins dependent on the co-translational secretion pathway. While not all sec71, sec72, sec62 or sec63 mutants will necessarily show a loss of halo phenotype with Siren-AMY fusions, the mutations obtained in these same loci using the loss of halo screen are a specific class effective and specific for siren signals (see Table 3). Thus, the transport of siren-fusions can be functionally separated from the transport of authentic signal sequences, despite the use of the same protein complex by both types of peptides. Mutant sec62 alleles can also provide a siren-sequence post-translational translocation defect while retaining significant transport of co-translationally secreted proteins.

From the present work, it is clear that the siren-sequences discovered herein are a new class of sequences that are recognized and transported by the post-translational translocation protein complex. Furthermore, siren-sequence translocation can be reduced or eliminated under suitable conditions or genetic backgrounds while maintaining transport of proteins via the co-translational secretion pathway. The use of a siren-sequence transport defective mutation in the genetic background of a host cell used to select or screen for secretion of authentic signal peptide containing reporter proteins, provides the advantage of improved efficiency by eliminating or reducing false positives, enriching for authentic signal peptides in the assay, and eliminates the time and cost required to analyze these misleading sequences.

What is claimed:

1. A method of detecting DNA comprising a coding sequence of a mammalian signal peptide which comprises:
   a) screening post-translational-translocation deficient, reporter-protein deficient yeast cells, transformed with DNA containing the coding sequence of a mammalian peptide ligated to DNA encoding the reporter protein lacking a functional native signal peptide, for their ability to secrete the reporter protein;
   wherein the DNA containing the coding sequence of a mammalian peptide in the transformed yeast cells which are able to secrete the reporter protein represents the DNA comprising a coding sequence of a mammalian signal peptide.

2. The method of claim 1, wherein the yeast cell comprises a post-translational translocation deficient allele of a gene encoding a post-translational translocation pathway protein.

3. The method of claim 2, wherein the yeast cell comprises a post-translational translocation deficient sec71 allele, sec72 allele, or sec62 allele.

4. The method of claim 3, wherein the sec71 allele is the truncated sec71 allele of SEQ ID NO:8.

5. The method of claim 1, wherein the yeast cell comprises an antisense molecule to a gene or RNA encoding a post-translational translocation pathway protein to reduce or prevent post-translational-translocation.

6. The method of claim 1, wherein the yeast cell post-translational translocation deficiency is non-revertible.

7. The method of claim 1 wherein the yeast is *Saccharomyces cerevisiae*.

8. The method of claim 1, wherein the reporter gene is invertase and the transformed yeast cells are selected for their ability to grow on sucrose or raffinose.

9. The method of claim 1, wherein the reporter gene is amylase, the yeast cells are non-amylolytic, and the transformed cells are screened for their ability to degrade starch.

10. The method of claim 9, wherein native amylase signal peptide is lacking and the amylase gene lacks a functional ATG or start condon at the N-terminus.

11. The method of claim 9, wherein the screening process is selected from the group consisting of: growth on selective media followed by replica plating onto YEPD-starch media; growth on selective media wherein starch is directly incorporate; and growth on selective media wherein starch bonded to visible dye is directly incorporated.

12. The method of claim 11, wherein the starch concentration is form about 0.5% to about 2.0%.

13. A method of detecting, in a mammalian recombinant DNA library, DNA encoding a secreted or transmembrane protein or an N-terminal fragment thereof, which comprises:
   a) screening post-translational-translocation deficient, reporter-gene deficient yeast cells, transformed with DNA obtained by the ligation of said mammalian recombinant DNA library to DNA encoding the reporter protein lacking a functional native signal peptide, for their ability to secrete the reporter protein;
   wherein the DNA of said mammalian recombinant DNA library in the transformed yeast cells which are able to secrete the reporter protein represents the DNA encoding a secreted or transmembrane protein or an N-terminal fragment thereof.

14. The method of claim 13, wherein the yeast cell comprises a post-translational translocation deficient allele of a gene encoding a post-translational translocation pathway protein.

15. The method of claim 13, wherein the reporter gene is invertase and the transformed yeast cells are selected for their ability to grow on sucrose or raffinose.

16. The method of claim 13, wherein the reporter gene is amylase, the yeast cells are non-amylolytic, and the transformed cells are screened for their ability opt degrade starch.

17. The method of claim 13 wherein the DNA is cDNA.

18. The method of claim 13 wherein the DNA is genomic DNA.

19. A method of detecting DNA comprising the coding sequence of a mammalian signal peptide which comprises:
   a) screening yeast cells for their ability to degrade starch, which:
      i) are amylolytic due to the presence of a starch degrading enzyme and post-translational-translocation deficient, but wherein
      ii) such cells have had the signal sequence associated with the starch degrading enzyme inactivated, and which have been
      iii) transformed with DNA containing the coding sequence of a mammalian peptide ligated to the DNA encoding the starch degrading enzyme, for their ability to degrade starch;
   wherein the DNA containing the coding sequence of a mammalian peptide in the transformed yeast cells which are able to degrade starch represents the DNA comprising the coding sequence of a mammalian signal peptide.

20. The method of claim 19, wherein the yeast cell comprises a post-translational translocation deficient allele of a gene encoding a post-translational translocation pathway protein.

21. The method of claim 19, wherein the starch degrading signal sequence is not present and the gene encoding the starch degrading enzyme lacks a functional ATG or start codon at the N-terminus.

22. A method of detecting, in a mammalian recombinant DNA library, DNA encoding a secreted or transmembrane protein or an N-terminal fragment thereof, which comprises:
   a) screening yeast cells for their ability to degrade starch which:
      i) are amylolytic due to the presence of a starch degrading enzyme and post-translational-translocation deficient, but wherein
      ii) such cells have had the signal sequence associated with the starch degrading enzyme inactivated, and which have been
      iii) transformed with DNA containing the coding sequence of a mammalian peptide ligated to the DNA encoding the starch degrading enzyme, for their ability to degrade starch;
   wherein the DNA containing the coding sequence of a mammalian peptide in the transformed yeast cells which are able to degrade starch represents the DNA encoding a secreted or transmembrane protein or an N-terminal fragment thereof.

23. The method of claim 22, wherein the yeast cell comprises a post-translational translocation deficient allele of a gene encoding a post-translational translocation pathway protein.

24. The method of claim 22, wherein the starch degrading signal sequence is not present and the gene encoding the starch degrading enzyme lacks a functional ATG or start codon at the N-terminus.

25. A host yeast cell comprising a post-translational translocation deficiency, a reporter protein deficiency, and a selectable plasmid-maintenance-marker-deficiency, wherein said reporter protein is selected from the group consisting of a starch degrading enzyme and invertase.

26. The yeast cell of claim 25, wherein the post-translational translocation deficiency comprises a posttranslational translocation deficient allele of a gene encoding a post-translational translocation pathway protein.

27. The yeast cell of claim 25, that further comprises a plasmid comprising a selectable marker for plasmid maintenance that complements the selectable plasmid-maintenance-marker-deficiency and a mammalian peptide-reporter protein fusion gene that complements the reporter protein deficiency.

28. A method of making the yeast cell of claim 26, comprising introducing into the genome of a yeast cell comprising a reporter protein deficiency and a selectable plasmid-maintenance-marker-deficiency and that is post-translational translocation efficient, a post-translational translocation deficient allele of a gene encoding a post-translational translocation pathway protein.

29. The method of claim 28, wherein the post-translational translocation deficient allele is obtained from a loss of halo screen using a siren-sequence/reporter gene fusion, wherein said siren sequence is selected from the group consisting of RS20, BTF3, EF11, P68 and ROA.

* * * * *

UNITED STATES PATENT AND TRADEMARK OFFICE
CERTIFICATE OF CORRECTION

PATENT NO. : 6,228,590 B1
DATED : May 8, 2001
INVENTOR(S) : Kevin P. Baker

It is certified that error appears in the above-identified patent and that said Letters Patent is hereby corrected as shown below:

Column 61,
Line 46, please delete "form" and insert -- from --.

Signed and Sealed this

Twenty-fifth Day of December, 2001

Attest:

*Attesting Officer*

JAMES E. ROGAN
*Director of the United States Patent and Trademark Office*

SEQUENCE LISTING

<160> NUMBER OF SEQ ID NOS: 10

<210> SEQ ID NO 1
<211> LENGTH: 7633
<212> TYPE: DNA
<213> ORGANISM: Artificial
<220> FEATURE:
<221> NAME/KEY: Artificial Sequence
<222> LOCATION: 1-7633
<223> OTHER INFORMATION: :/note=plasmid pSST-AMY.1

<400> SEQUENCE: 1

```
gccggctttc cccgtcaagc tctaaatcgg gggctcccctt tagggttccg        50
atttagtgct ttacggcacc tcgaccccaa aaaacttgat tagggtgatg        100
gttcacgtag tgggccatcg ccctgataga cggttttcg  ccctttgacg        150
ttggagtcca cgttctttaa tagtggactc ttgttccaaa ctgaacaac         200
actcaaccct atctcggtct attcttttga tttataaggg attttgccga        250
tttcggccta ttggttaaaa aatgagctga tttaacaaaa atttaacgcg        300
aattttaaca aaatattaac gcttacaatt tccattcgcc attcaggctg        350
cgcaactgtt gggaagggcg atcggtgcgg gcctcttcgc tattacgcca        400
gctggcgaaa gggggatgtg ctgcaaggcg attaagttgg gtaacgccag        450
ggttttccca gtcacgacgt tgtaaaacga cggccagtga attgtaatac        500
gactcactat agggcgaatt gggtaccggg ccccccctcg aggcttagcg        550
atgcttcgtt gcttgcatgc aacttctttt ctttttttt cttttctctc         600
tccccgttg ttgtctcacc atatccgcaa tgacaaaaaa aatgatggaa          650
gacactaaag gaaaaaatta acgacaaaga cagcaccaac agatgtcgtt        700
gttccagagc tgatgagggg tatcttcgaa cacacgaaac tttttccttc        750
cttcattcac gcacactact ctctaatgag caacggtata cggccttcct        800
```

```
tccagttact tgaatttgaa ataaaaaaag tttgccgctt tgctatcaag        850
tataaataga cctgcaatta ttaatctttt gtttcctcgt cattgttctc        900
gttccctttc ttccttgttt ctttttctgc acaatatttc aagctatacc        950
aagcatacaa tcaactccaa gctatcgata ggccacactg gccgtcgacg       1000
cggccgctgg ggtatctctc gagaaaagag aggcccaata tgacccacat       1050
actcaatatg gacgaactgc tattatccac ctgtttgagt ggcgctgggt       1100
tgatattgct aaggaatgtg agagatactt agctcctaat ggatttgcag       1150
gtgtgcaggt ctctccaccc aatgaaaaca tcgtagtcca cagcccttca       1200
agaccatggt gggaaagata tcaaccaatt agctacaaaa tatgttccag       1250
gtctggaaat gaagatgaat tcagggacat ggtgaacagg tgcaacaatg       1300
ttggtgtccg tatttatgtg gatgctgtca ttaaccacat gtgtggagtg       1350
ggggctcaag ctggacaaag cagtacatgt ggaagttatt tcaacccaaa       1400
taacagggac tttcctggag ttccctattc tggttttgac tttaatgatg       1450
gaaaatgtag aactgcaagt ggaggtatcg agaactacca agatgctgct       1500
caggtcgaga ttgtcgtct gtctggcctt ctggatcttg cacttgagaa        1550
agattatgtt cgaaccaagg tggctgacta tatgaaccat ctcattgaca       1600
ttggcgtagc agggttcaga cttgatgctt ctaagcacat gtggcctgga       1650
gacataaagg caattttgga caaactgcat aatctcaata caaaatggtt       1700
ctcccaagga agcagaccct tcatttttcca gaggtgatt gatctgggtg       1750 gtgaggcagt gtcaagtaat gagtattttg gaaatggccg tgtgacagaa       1800
ttcaaatatg gagcaaaatt gggcaaagtt atgcgcaagt gggatggaga       1850
aaagatgtcc tacttaaaga actggggaga aggttggggt ttgatgcctt       1900 ctgcacagagc ccttgtgttt gtggacaacc atgacaatca gcgaggacat      1950
ggtgctgggg gagcatccat cttgacattc tgggatgcta gactctataa       2000
aatggctgtt ggctttatgt tggctcatcc ttatggtttc acacgggtga       2050
tgtcaagtta ctattggcca agaaatttcc agaatggaaa agatgtcaat       2100
gactgggttg gaccaccaaa taacaatgga aaaaccaaag aagtgagcat       2150
taacccagac agcacttgtg gcaatgactg gatctgtgaa caccgatggc       2200
gtcaaataag gaacatggtt gccttcagaa atgtcgtcaa tggtcagcct       2250 tttgcaaaact ggtgggataa tgcagcaac caggtagctt ttggcagagg      2300
aaacaaagga ctcattgtct ttaacaatga tgactgggct ttgtcagaaa       2350
ctttacagac tggtcttcct gctggcacat actgtgatgt catttctgga       2400
gataaagtcg atggcaattg cactggaata aaagtctatg ttggcaatga       2450 tgcaaagct cactttccta ttagtaactc tgccgaagac ccatttattg        2500
caatccatgc agagtcaaaa atataaggat ccgcggaagc tttggacttc       2550
ttcgccagag gtttggtcaa gtctccaatc aaggttgtcg gcttgtctac       2600
cttgccagaa atttacgaaa agatggaaaa gggtcaaatc gttggtagat       2650
acgttgttga cacttctaaa taagcgaatt tcttatgatt tatgattttt       2700
attattaaat aagttatata aaaaataagt gtatacaaat tttaaagtga       2750
```

| | |
|---|---|
| ctcttaggtt ttaaaacgaa aattcttgtt cttgagtaac tctttcctgt | 2800 |
| aggtcaggtt gctttctcag gtatagcatg aggtcgctct tattgaccac | 2850 |
| acctctaccg gcatgcgaat tcgagctcgg tacccgggta ataactgata | 2900 |
| taattaaatt gaagctctaa tttgtgagtt tagtatacat gcatttactt | 2950 |
| ataatacagt tttttagttt tgctggccgc atcttctcaa atatgcttcc | 3000 |
| cagcctgctt ttctgtaacg ttcaccctct accttagcat cccttccctt | 3050 |
| tgcaaatagt cctcttccaa caataataat gtcagatcct gtagagacca | 3100 |
| catcatccac ggttctatac tgttgaccca atgcgtctcc cttgtcatct | 3150 |
| aaacccacac cgggtgtcat aatcaaccaa tcgtaacctt catctcttcc | 3200 |
| acccatgtct ctttgagcaa taaagccgat aacaaaatct ttgtcgctct | 3250 |
| tcgcaatgtc aacagtaccc ttagtatatt ctccagtaga tagggagccc | 3300 |
| ttgcatgaca attctgctaa catcaaaagg cctctaggtt cctttgttac | 3350 |
| ttcttctgcc gcctgcttca aaccgctaac aatacctggg cccaccacac | 3400 |
| cgtgtgcatt cgtaatgtct gcccattctg ctattctgta tacacccgca | 3450 |
| gagtactgca atttgactgt attaccaatg tcagcaaatt ttctgtcttc | 3500 |
| gaagagtaaa aaattgtact tggcggataa tgcctttagc ggcttaactg | 3550 |
| tgccctccat ggaaaaatca gtcaagatat ccacatgtgt ttttagtaaa | 3600 |
| caaattttgg gacctaatgc ttcaactaac tccagtaatt ccttggtggt | 3650 |
| acgaacatcc aatgaagcac acaagtttgt ttgcttttcg tgcatgatat | 3700 |
| taaatagctt ggcagcaaca ggactaggat gagtagcagc acgttcctta | 3750 |
| tatgtagctt tcgacatgat ttatcttcgt ttcctgcagg ttttttgttct | 3800 |
| gtgcagttgg gttaagaata ctgggcaatt tcatgtttct tcaacactac | 3850 |
| atatgcgtat atataccaat ctaagtctgt gctccttcct tcgttcttcc | 3900 |
| ttctgttcgg agattaccga atcaaaaaaa tttcaaggaa accgaaatca | 3950 |
| aaaaaagaa taaaaaaaaa atgatgaatt gaaaagctta cattttatgt | 4000 |
| tagctggtgg actgacgcca gaaaatgttg gtgatgcgct tagattaaat | 4050 |
| ggcgttattg gtgttgatgt aagcggaggt gtggagacaa atggtgtaaa | 4100 |
| agactctaac aaaatagcaa atttcgtcaa aaatgctaag aaataggtta | 4150 |
| ttactgagta gtatttattt aagtattgtt tgtgcacttg cctgcaggcc | 4200 |
| ttttgaaaag caagcataaa agatctaaac ataaaatctg taaaataaca | 4250 |
| agatgtaaag ataatgctaa atcatttggc ttttgattg attgtacagg | 4300 |
| aaaatataca tcgcagggg ttgactttta ccatttcacc gcaatggaat | 4350 |
| caaacttgtt gaagagaatg ttcacaggcg catacgctac aatgacccga | 4400 |
| ttcttgctag ccttttctcg gtcttgcaaa caaccgccaa ctctaagagg | 4450 |
| tgatacttat ttactgtaaa actgtgacga taaaaccgga aggaagaata | 4500 |
| agaaaactcg aactgatcta taatgcctat tttctgtaaa gagtttaagc | 4550 |
| tatgaaagcc tcggcatttt ggccgctcct aggtagtgct ttttttccaa | 4600 |
| ggacaaaaca gtttcttttt cttgagcagg ttttatgttt cggtaatcat | 4650 |
| aaacaataaa taaattattt catttatgtt taaaaataaa aataaaaaa | 4700 |
| gtattttaaa ttttttaaaaa agttgattat aagcatgtga ccttttgcaa | 4750 |

-continued

```
gcaattaaat tttgcaattt gtgattttag gcaaaagtta caatttctgg          4800
ctcgtgtaat atatgtatgc taaagtgaac ttttacaaag tcgatatgga          4850
cttagtcaaa agaaattttc ttaaaaatat atagcactag ccaatttagc          4900
acttctttat gagatatatt atagacttta ttaagccaga tttgtgtatt          4950
atatgtattt acccggcgaa tcatggacat acattctgaa ataggtaata          5000
ttctctatgg tgagacagca tagataacct aggatacaag ttaaaagcta          5050
gtactgtttt gcagtaattt ttttcttttt tataagaatg ttaccaccta          5100
aataagttat aaagtcaata gttaagtttg atatttgatt gtaaaatacc          5150
gtaatatatt tgcatgatca aaaggctcaa tgttgactag ccagcatgtc          5200
aaccactata ttgatcaccg atatatggac ttccacacca actagtaata          5250
tgacaataaa ttcaagatat tcttcatgag aatgggccca ctgcctcgcg          5300
cgtttcggtg atgacggtga aaacctctga cacatgcagc tcccggagac          5350
ggtcacagct tgtctgtaag cggatgccgg gagcagacaa gcccgtcagg          5400
gcgcgtcagc gggtgttggc gggtgtcggg gcgcagccat gacccagtca          5450
cgtagcgata gcggagtgta tactggctta actatgcggc atcagagcag          5500
attgtactga gagtgcacca tatgcggtgt gaaataccgc acagatgcgt          5550
aaggagaaaa taccgcatca ggcgctcttc cgcttcctcg ctcactgact          5600
cgctgcgctc ggtcgttcgg ctgcggcgag cggtatcagc tcactcaaag          5650
gcggtaatac ggttatccac agaatcaggg gataacgcag gaaagaacat          5700
gtgagcaaaa ggccagcaaa aggccaggaa ccgtaaaaag gccgcgttgc          5750
tggcgttttt ccataggctc cgcccccctg acgagcatca caaaaatcga          5800
cgctcaagtc agaggtggcg aaacccgaca ggactataaa gataccaggc          5850
gtttccccct ggaagctccc tcgtgcgctc tcctgttccg accctgccgc          5900
ttaccggata cctgtccgcc tttctccctt cgggaagcgt ggcgctttct          5950
catagctcac gctgtaggta tctcagttcg gtgtaggtcg ttcgctccaa          6000
gctgggctgt gtgcacgaac cccccgttca gcccgaccgc tgcgccttat          6050
ccggtaacta tcgtcttgag tccaacccgg taagacacga cttatcgcca          6100
ctggcagcag ccactggtaa caggattagc agagcgaggt atgtaggcgg          6150
tgctacagag ttcttgaagt ggtggcctaa ctacggctac actagaagga          6200
cagtatttgg tatctgcgct ctgctgaagc cagttacctt cggaaaaaga          6250
gttggtagct cttgatccgg caaacaaacc accgctggta gcggtggttt          6300
ttttgtttgc aagcagcaga ttacgcgcag aaaaaaagga tctcaagaag          6350
atcctttgat cttttctacg gggtctgacg ctcagtggaa cgaaaactca          6400
cgttaaggga ttttggtcat gagattatca aaaaggatct tcacctagat          6450
ccttttaaat taaaaatgaa gttttaaatc aatctaaagt atatatgagt          6500
aaacttggtc tgacagttac caatgcttaa tcagtgaggc acctatctca          6550
gcgatctgtc tatttcgttc atccatagtt gcctgactcc ccgtcgtgta          6600
gataactacg atacgggagg gcttaccatc tggccccagt gctgcaatga          6650
taccgcgaga cccacgctca ccggctccag atttatcagc aataaaccag          6700
```

-continued

| | |
|---|---|
| ccagccggaa gggccgagcg cagaagtggt cctgcaactt tatccgcctc | 6750 |
| catccagtct attaattgtt gccgggaagc tagagtaagt agttcgccag | 6800 |
| ttaatagttt gcgcaacgtt gttgccattg ctgcaggcat cgtggtgtca | 6850 |
| cgctcgtcgt ttggtatggc ttcattcagc tccggttccc aacgatcaag | 6900 |
| gcgagttaca tgatccccca tgttgtgcaa aaaagcggtt agctccttcg | 6950 |
| gtcctccgat cgttgtcaga agtaagttgg ccgcagtgtt atcactcatg | 7000 |
| gttatggcag cactgcataa ttctcttact gtcatgccat ccgtaagatg | 7050 |
| cttttctgtg actggtgagt actcaaccaa gtcattctga aatagtgta | 7100 |
| tgcggcgacc gagttgctct tgcccggcgt caacacggga taataccgcg | 7150 |
| ccacatagca gaactttaaa agtgctcatc attggaaaac gttcttcggg | 7200 |
| gcgaaaactc tcaaggatct taccgctgtt gagatccagt tcgatgtaac | 7250 |
| ccactcgtgc acccaactga tcttcagcat cttttacttt caccagcgtt | 7300 |
| tctgggtgag caaaaacagg aaggcaaaat gccgcaaaaa agggaataag | 7350 |
| ggcgacacgg aaatgttgaa tactcatact cttcctttt caatattatt | 7400 |
| gaagcattta tcagggttat tgtctcatga gcggatacat atttgaatgt | 7450 |
| atttagaaaa ataaacaaat aggggttccg cgcacatttc cccgaaaagt | 7500 |
| gccacctgac gcgccctgta gcggcgcatt aagcgcggcg ggtgtggtgg | 7550 |
| ttacgcgcag cgtgaccgct acacttgcca gcgccctagc gcccgctcct | 7600 |
| ttcgctttct tcccttcctt tctcgccacg ttc | 7633 |

<210> SEQ ID NO 2
<211> LENGTH: 43
<212> TYPE: DNA
<213> ORGANISM: Artificial
<220> FEATURE:
<221> NAME/KEY: Artificial Sequence
<222> LOCATION: 1-43
<223> OTHER INFORMATION: :/note=Synthetic

<400> SEQUENCE: 2
tgtaaaacga cggccagtta aatagacctg caattattaa tct       43

<210> SEQ ID NO 3
<211> LENGTH: 41
<212> TYPE: DNA
<213> ORGANISM: Artificial
<220> FEATURE:
<221> NAME/KEY: Artificial Sequence
<222> LOCATION: 1-41
<223> OTHER INFORMATION: :/note=Synthetic

<400> SEQUENCE: 3
caggaaacag ctatgaccac ctgcacacct gcaaatccat t         41

<210> SEQ ID NO 4
<211> LENGTH: 627
<212> TYPE: PRT
<213> ORGANISM: Artificial
<220> FEATURE:
<221> NAME/KEY: Artificial Sequence
<222> LOCATION: 1-627
<223> OTHER INFORMATION: :/note=plasmid RS20-AMY

<400> SEQUENCE: 4

Met Ala Phe Lys Asp Thr Gly Lys Thr Pro Val Glu Pro Glu Val

-continued

```
  1               5                  10                 15
Ala Ile His Arg Ile Arg Ile Thr Leu Thr Ser Arg Asn Val Lys
                20                 25                 30
Ser Leu Glu Lys Val Cys Ala Asp Leu Ile Arg Gly Ala Lys Glu
                35                 40                 45
Lys Asn Leu Lys Val Lys Gly Pro Val Arg Met Pro Thr Lys Thr
                50                 55                 60
Leu Arg Ile Thr Thr Arg Lys Thr Pro Cys Gly Glu Gly Ser Lys
                65                 70                 75
Thr Trp Asp Arg Phe Gln Met Arg Ile His Lys Arg Leu Ile Asp
                80                 85                 90
Leu His Ser Pro Ser Glu Ile Val Lys Gln Ile Thr Ser Ile Ser
                95                100                105
Ile Glu Pro Gly Ala Ser Ala Asn His Val Ala Ala Ala Asn Trp
               110                115                120
Ala Ala Gly Val Ser Leu Glu Lys Arg Glu Ala Gln Tyr Asp Pro
               125                130                135
His Thr Gln Tyr Gly Arg Thr Ala Ile Ile His Leu Phe Glu Trp
               140                145                150
Arg Trp Val Asp Ile Ala Lys Glu Cys Glu Arg Tyr Leu Ala Pro
               155                160                165
Asn Gly Phe Ala Gly Val Gln Val Ser Pro Pro Asn Glu Asn Ile
               170                175                180
Val Val His Ser Pro Ser Arg Pro Trp Trp Glu Arg Tyr Gln Pro
               185                190                195
Ile Ser Tyr Lys Ile Cys Ser Arg Ser Gly Asn Glu Asp Glu Phe
               200                205                210
Arg Asp Met Val Asn Arg Cys Asn Asn Val Gly Val Arg Ile Tyr
               215                220                225
Val Asp Ala Val Ile Asn His Met Cys Gly Val Gly Ala Gln Ala
               230                235                240
Gly Gln Ser Ser Thr Cys Gly Ser Tyr Phe Asn Pro Asn Asn Arg
               245                250                255
Asp Phe Pro Gly Val Pro Tyr Ser Gly Phe Asp Phe Asn Asp Gly
               260                265                270
Lys Cys Arg Thr Ala Ser Gly Gly Ile Glu Asn Tyr Gln Asp Ala
               275                280                285
Ala Gln Val Arg Asp Cys Arg Leu Ser Gly Leu Leu Asp Leu Ala
               290                295                300
Leu Glu Lys Asp Tyr Val Arg Thr Lys Val Ala Asp Tyr Met Asn
               305                310                315
His Leu Ile Asp Ile Gly Val Ala Gly Phe Arg Leu Asp Ala Ser
               320                325                330
Lys His Met Trp Pro Gly Asp Ile Lys Ala Ile Leu Asp Lys Leu
               335                340                345
His Asn Leu Asn Thr Lys Trp Phe Ser Gln Gly Ser Arg Pro Phe
               350                355                360
Ile Phe Gln Glu Val Ile Asp Leu Gly Gly Glu Ala Val Ser Ser
               365                370                375
Asn Glu Tyr Phe Gly Asn Gly Arg Val Thr Glu Phe Lys Tyr Gly
               380                385                390
Ala Lys Leu Gly Lys Val Met Arg Lys Trp Asp Gly Glu Lys Met
               395                400                405
```

```
Ser Tyr Leu Lys Asn Trp Gly Glu Gly Trp Gly Leu Met Pro Ser
                410                 415                 420

Asp Arg Ala Leu Val Phe Val Asp Asn His Asp Asn Gln Arg Gly
                425                 430                 435

His Gly Ala Gly Gly Ala Ser Ile Leu Thr Phe Trp Asp Ala Arg
                440                 445                 450

Leu Tyr Lys Met Ala Val Gly Phe Met Leu Ala His Pro Tyr Gly
                455                 460                 465

Phe Thr Arg Val Met Ser Ser Tyr Tyr Trp Pro Arg Asn Phe Gln
                470                 475                 480

Asn Gly Lys Asp Val Asn Asp Trp Val Gly Pro Pro Asn Asn Asn
                485                 490                 495

Gly Lys Thr Lys Glu Val Ser Ile Asn Pro Asp Ser Thr Cys Gly
                500                 505                 510

Asn Asp Trp Ile Cys Glu His Arg Trp Arg Gln Ile Arg Asn Met
                515                 520                 525

Val Ala Phe Arg Asn Val Val Asn Gly Gln Pro Phe Ala Asn Trp
                530                 535                 540

Trp Asp Asn Asp Ser Asn Gln Val Ala Phe Gly Arg Gly Asn Lys
                545                 550                 555

Gly Leu Ile Val Phe Asn Asn Asp Asp Trp Ala Leu Ser Glu Thr
                560                 565                 570

Leu Gln Thr Gly Leu Pro Ala Gly Thr Tyr Cys Asp Val Ile Ser
                575                 580                 585

Gly Asp Lys Val Asp Gly Asn Cys Thr Gly Ile Lys Val Tyr Val
                590                 595                 600

Gly Asn Asp Gly Lys Ala His Phe Ser Ile Ser Asn Ser Ala Glu
                605                 610                 615

Asp Pro Phe Ile Ala Ile His Ala Glu Ser Lys Ile
                620                 625     627

<210> SEQ ID NO 5
<211> LENGTH: 525
<212> TYPE: PRT
<213> ORGANISM: Artificial
<220> FEATURE:
<221> NAME/KEY: Artificial Sequence
<222> LOCATION: 1-525
<223> OTHER INFORMATION: :/note=plasmid RL15-AMY

<400> SEQUENCE: 5

Met Leu Cys Gln Ile Lys Lys Val Lys Val Gln Ser Arg Ala Ala
 1               5                  10                  15

Ala Asn Trp Ala Ala Gly Val Ser Leu Glu Lys Arg Glu Ala Gln
                20                  25                  30

Tyr Asp Pro His Thr Gln Tyr Gly Arg Thr Ala Ile Ile His Leu
                35                  40                  45

Phe Glu Trp Arg Trp Val Asp Ile Ala Lys Glu Cys Glu Arg Tyr
                50                  55                  60

Leu Ala Pro Asn Gly Phe Ala Gly Val Gln Val Ser Pro Pro Asn
                65                  70                  75

Glu Asn Ile Val Val His Ser Pro Ser Arg Pro Trp Trp Glu Arg
                80                  85                  90

Tyr Gln Pro Ile Ser Tyr Lys Ile Cys Ser Arg Ser Gly Asn Glu
                95                  100                 105
```

-continued

```
Asp Glu Phe Arg Asp Met Val Asn Arg Cys Asn Asn Val Gly Val
                110                 115                 120

Arg Ile Tyr Val Asp Ala Val Ile Asn His Met Cys Gly Val Gly
            125                 130                 135

Ala Gln Ala Gly Gln Ser Ser Thr Cys Gly Ser Tyr Phe Asn Pro
        140                 145                 150

Asn Asn Arg Asp Phe Pro Gly Val Pro Tyr Ser Gly Phe Asp Phe
    155                 160                 165

Asn Asp Gly Lys Cys Arg Thr Ala Ser Gly Gly Ile Glu Asn Tyr
170                 175                 180

Gln Asp Ala Ala Gln Val Arg Asp Cys Arg Leu Ser Gly Leu Leu
                185                 190                 195

Asp Leu Ala Leu Glu Lys Asp Tyr Val Arg Thr Lys Val Ala Asp
            200                 205                 210

Tyr Met Asn His Leu Ile Asp Ile Gly Val Ala Gly Phe Arg Leu
        215                 220                 225

Asp Ala Ser Lys His Met Trp Pro Gly Asp Ile Lys Ala Ile Leu
    230                 235                 240

Asp Lys Leu His Asn Leu Asn Thr Lys Trp Phe Ser Gln Gly Ser
245                 250                 255

Arg Pro Phe Ile Phe Gln Glu Val Ile Asp Leu Gly Gly Glu Ala
                260                 265                 270

Val Ser Ser Asn Glu Tyr Phe Gly Asn Gly Arg Val Thr Glu Phe
            275                 280                 285

Lys Tyr Gly Ala Lys Leu Gly Lys Val Met Arg Lys Trp Asp Gly
        290                 295                 300

Glu Lys Met Ser Tyr Leu Lys Asn Trp Gly Glu Gly Trp Gly Leu
    305                 310                 315

Met Pro Ser Asp Arg Ala Leu Val Phe Val Asp Asn His Asp Asn
320                 325                 330

Gln Arg Gly His Gly Ala Gly Gly Ala Ser Ile Leu Thr Phe Trp
                335                 340                 345

Asp Ala Arg Leu Tyr Lys Met Ala Val Gly Phe Met Leu Ala His
            350                 355                 360

Pro Tyr Gly Phe Thr Arg Val Met Ser Ser Tyr Tyr Trp Pro Arg
        365                 370                 375

Asn Phe Gln Asn Gly Lys Asp Val Asn Asp Trp Val Gly Pro Pro
    380                 385                 390

Asn Asn Asn Gly Lys Thr Lys Glu Val Ser Ile Asn Pro Asp Ser
395                 400                 405

Thr Cys Gly Asn Asp Trp Ile Cys Glu His Arg Trp Arg Gln Ile
                410                 415                 420

Arg Asn Met Val Ala Phe Arg Asn Val Val Asn Gly Gln Pro Phe
            425                 430                 435

Ala Asn Trp Trp Asp Asn Asp Ser Asn Gln Val Ala Phe Gly Arg
        440                 445                 450

Gly Asn Lys Gly Leu Ile Val Phe Asn Asn Asp Asp Trp Ala Leu
    455                 460                 465

Ser Glu Thr Leu Gln Thr Gly Leu Pro Ala Gly Thr Tyr Cys Asp
470                 475                 480

Val Ile Ser Gly Asp Lys Val Asp Gly Asn Cys Thr Gly Ile Lys
                485                 490                 495

Val Tyr Val Gly Asn Asp Gly Lys Ala His Phe Ser Ile Ser Asn
```

```
                       500               505               510
Ser Ala Glu Asp Pro Phe Ile Ala Ile His Ala Glu Ser Lys Ile
                515               520               525

<210> SEQ ID NO 6
<211> LENGTH: 660
<212> TYPE: PRT
<213> ORGANISM: Artificial
<220> FEATURE:
<221> NAME/KEY: Artificial Sequence
<222> LOCATION: 1-660
<223> OTHER INFORMATION: :/note=plasmid PERT-AMY
<220> FEATURE:
<221> NAME/KEY: unknown
<222> LOCATION: 90, 98
<223> OTHER INFORMATION: unknown amino acid

<400> SEQUENCE: 6

Met Arg Ala Leu Ala Val Leu Ser Val Thr Leu Val Met Ala Cys
  1               5                  10                  15

Thr Glu Ala Phe Phe Pro Phe Ile Ser Arg Gly Lys Asn Ser Phe
                 20                  25                  30

Trp Gly Lys Ala Glu Glu Ser Arg Val Ser Ser Val Leu Glu Glu
                 35                  40                  45

Ser Lys Arg Leu Val Asp Thr Ala Met Tyr Ala Thr Met Gln Arg
                 50                  55                  60

Asn Leu Lys Lys Arg Gly Ile Leu Ser Pro Ala Gln Leu Leu Ser
                 65                  70                  75

Phe Ser Lys Leu Pro Glu Pro Thr Ser Gly Val Ile Ala Arg Xaa
                 80                  85                  90

Ala Glu Ile Met Glu Thr Ser Xaa Gln Ala Met Lys Arg Lys Val
                 95                 100                 105

Asn Leu Lys Thr Gln Gln Ser Gln His Pro Thr Asp Ala Leu Ser
                110                 115                 120

Glu Asp Leu Leu Ser Ile Ile Ala Asn Met Ser Gly Cys Leu Pro
                125                 130                 135

Tyr Met Leu Pro Pro Lys Cys Pro Asn Thr Cys His Val Ala Ala
                140                 145                 150

Ala Asn Trp Ala Ala Gly Val Ser Leu Glu Lys Arg Glu Ala Gln
                155                 160                 165

Tyr Asp Pro His Thr Gln Tyr Gly Arg Thr Ala Ile Ile His Leu
                170                 175                 180

Phe Glu Trp Arg Trp Val Asp Ile Ala Lys Glu Cys Glu Arg Tyr
                185                 190                 195

Leu Ala Pro Asn Gly Phe Ala Gly Val Gln Val Ser Pro Pro Asn
                200                 205                 210

Glu Asn Ile Val Val His Ser Pro Ser Arg Pro Trp Trp Glu Arg
                215                 220                 225

Tyr Gln Pro Ile Ser Tyr Lys Ile Cys Ser Arg Ser Gly Asn Glu
                230                 235                 240

Asp Glu Phe Arg Asp Met Val Asn Arg Cys Asn Asn Val Gly Val
                245                 250                 255

Arg Ile Tyr Val Asp Ala Val Ile Asn His Met Cys Gly Val Gly
                260                 265                 270

Ala Gln Ala Gly Gln Ser Ser Thr Cys Gly Ser Tyr Phe Asn Pro
                275                 280                 285

Asn Asn Arg Asp Phe Pro Gly Val Pro Tyr Ser Gly Phe Asp Phe
```

-continued

```
                         290                 295                 300
Asn Asp Gly Lys Cys Arg Thr Ala Ser Gly Gly Ile Glu Asn Tyr
                 305                 310                 315
Gln Asp Ala Ala Gln Val Arg Asp Cys Arg Leu Ser Gly Leu Leu
                 320                 325                 330
Asp Leu Ala Leu Glu Lys Asp Tyr Val Arg Thr Lys Val Ala Asp
                 335                 340                 345
Tyr Met Asn His Leu Ile Asp Ile Gly Val Ala Gly Phe Arg Leu
                 350                 355                 360
Asp Ala Ser Lys His Met Trp Pro Gly Asp Ile Lys Ala Ile Leu
                 365                 370                 375
Asp Lys Leu His Asn Leu Asn Thr Lys Trp Phe Ser Gln Gly Ser
                 380                 385                 390
Arg Pro Phe Ile Phe Gln Glu Val Ile Asp Leu Gly Gly Glu Ala
                 395                 400                 405
Val Ser Ser Asn Glu Tyr Phe Gly Asn Gly Arg Val Thr Glu Phe
                 410                 415                 420
Lys Tyr Gly Ala Lys Leu Gly Lys Val Met Arg Lys Trp Asp Gly
                 425                 430                 435
Glu Lys Met Ser Tyr Leu Lys Asn Trp Gly Glu Gly Trp Gly Leu
                 440                 445                 450
Met Pro Ser Asp Arg Ala Leu Val Phe Val Asp Asn His Asp Asn
                 455                 460                 465
Gln Arg Gly His Gly Ala Gly Gly Ala Ser Ile Leu Thr Phe Trp
                 470                 475                 480
Asp Ala Arg Leu Tyr Lys Met Ala Val Gly Phe Met Leu Ala His
                 485                 490                 495
Pro Tyr Gly Phe Thr Arg Val Met Ser Ser Tyr Tyr Trp Pro Arg
                 500                 505                 510
Asn Phe Gln Asn Gly Lys Asp Val Asn Asp Trp Val Gly Pro Pro
                 515                 520                 525
Asn Asn Asn Gly Lys Thr Lys Glu Val Ser Ile Asn Pro Asp Ser
                 530                 535                 540
Thr Cys Gly Asn Asp Trp Ile Cys Glu His Arg Trp Arg Gln Ile
                 545                 550                 555
Arg Asn Met Val Ala Phe Arg Asn Val Val Asn Gly Gln Pro Phe
                 560                 565                 570
Ala Asn Trp Trp Asp Asn Asp Ser Asn Gln Val Ala Phe Gly Arg
                 575                 580                 585
Gly Asn Lys Gly Leu Ile Val Phe Asn Asn Asp Asp Trp Ala Leu
                 590                 595                 600
Ser Glu Thr Leu Gln Thr Gly Leu Pro Ala Gly Thr Tyr Cys Asp
                 605                 610                 615
Val Ile Ser Gly Asp Lys Val Asp Gly Asn Cys Thr Gly Ile Lys
                 620                 625                 630
Val Tyr Val Gly Asn Asp Gly Lys Ala His Phe Ser Ile Ser Asn
                 635                 640                 645
Ser Ala Glu Asp Pro Phe Ile Ala Ile His Ala Glu Ser Lys Ile
                 650                 655                 660
```

<210> SEQ ID NO 7
<211> LENGTH: 206
<212> TYPE: PRT
<213> ORGANISM: Saccharomyces cerevisiae

```
<400> SEQUENCE: 7

Met Ser Glu Phe Asn Glu Thr Lys Phe Ser Asn Asn Gly Thr Phe
 1               5                  10                  15

Phe Glu Thr Glu Glu Pro Ile Val Glu Thr Lys Ser Ile Ser Val
                 20                  25                  30

Tyr Thr Pro Leu Ile Tyr Val Phe Ile Leu Val Val Ser Leu Val
                 35                  40                  45

Met Phe Ala Ser Ser Tyr Arg Lys Lys Gln Ala Lys Lys Ile Ser
                 50                  55                  60

Glu Gln Pro Ser Ile Phe Asp Glu Asn Asp Ala His Asp Leu Tyr
                 65                  70                  75

Phe Gln Ile Lys Glu Met Ser Glu Asn Glu Lys Ile His Glu Lys
                 80                  85                  90

Val Leu Lys Ala Ala Leu Leu Asn Arg Gly Ala Glu Ser Val Arg
                 95                 100                 105

Arg Ser Leu Lys Leu Lys Glu Leu Ala Pro Gln Ile Asn Leu Leu
                110                 115                 120

Tyr Lys Asn Gly Ser Ile Gly Glu Asp Tyr Trp Lys Arg Phe Glu
                125                 130                 135

Thr Glu Val Lys Leu Ile Glu Leu Glu Phe Lys Asp Thr Leu Gln
                140                 145                 150

Glu Ala Glu Arg Leu Gln Pro Gly Trp Val Gln Leu Phe Val Met
                155                 160                 165

Val Cys Lys Glu Ile Cys Phe Asn Gln Ala Leu Ser Arg Arg Tyr
                170                 175                 180

Gln Ser Ile Leu Lys Arg Lys Glu Val Cys Ile Lys Glu Trp Glu
                185                 190                 195

Leu Lys Ile Asn Asn Asp Gly Arg Leu Val Asn
                200                 205 206

<210> SEQ ID NO 8
<211> LENGTH: 134
<212> TYPE: PRT
<213> ORGANISM: Saccharomyces cerevisiae

<400> SEQUENCE: 8

Met Ser Glu Phe Asn Glu Thr Lys Phe Ser Asn Asn Gly Thr Phe
 1               5                  10                  15

Phe Glu Thr Glu Glu Pro Ile Val Glu Thr Lys Ser Ile Ser Val
                 20                  25                  30

Tyr Thr Pro Leu Ile Tyr Val Phe Ile Leu Val Val Ser Leu Val
                 35                  40                  45

Met Phe Ala Ser Ser Tyr Arg Lys Lys Gln Ala Lys Lys Ile Ser
                 50                  55                  60

Glu Gln Pro Ser Ile Phe Asp Glu Asn Asp Ala His Asp Leu Tyr
                 65                  70                  75

Phe Gln Ile Lys Glu Met Ser Glu Asn Glu Lys Ile His Glu Lys
                 80                  85                  90

Val Leu Lys Ala Ala Leu Leu Asn Arg Gly Ala Glu Ser Val Arg
                 95                 100                 105

Arg Ser Leu Lys Leu Lys Glu Leu Ala Pro Gln Ile Asn Leu Leu
                110                 115                 120

Tyr Lys Lys Trp Leu Tyr Trp Gly Gly Leu Leu Glu Glu Ile
```

<210> SEQ ID NO 9
<211> LENGTH: 1684
<212> TYPE: DNA
<213> ORGANISM: Saccharomyces cerevisiae

<400> SEQUENCE: 9

| | | | | | |
|---|---|---|---|---|---|
| acgccaagct | tgcatgccag | catgtcaccg | tgctttagtc | ctagatccat | 50 |
| cactgttcga | tcagctagtt | cagaaacagc | atgaatacct | tgaccgggct | 100 |
| tctcacaaac | agtaaatgtg | tcgacatcgg | cattgggtc | cagattaccc | 150 |
| accaactttt | caatgaccgt | tccgaaaagg | tcgttttctt | gacaagaaac | 200 |
| cctgtgtgta | ccgttttttg | atctaaatct | gataagcata | cttcacttaa | 250 |
| atgtatatcg | atatcagtag | tatagggaaa | tttttcttca | gagtactgtc | 300 |
| ctattatttg | ccactcttcg | ttctgtatgt | tacgagggcg | ttccttaaaa | 350 |
| tgggtagacg | catcttatta | cccgccaaaa | aacgtcaaaa | gttttaggaa | 400 |
| cacgtctaaa | agttgaaata | atatgtgaaa | aaattgatga | aatattaatg | 450 |
| aaatggctta | tttaaacgaa | ttcaagtaca | ggaaagaggt | acgcacaact | 500 |
| acttgagttt | gccaatatgt | ccgaatttaa | tgaaacaaaa | ttctccaaca | 550 |
| acgggacgtt | ttttgaaacg | gaagagccaa | ttgtggagac | gaaatcaatc | 600 |
| tccgtttata | ccccactcat | atatgtcttt | attctggtgg | tgtcccttgt | 650 |
| gatgtttgct | tcaagctaca | gaaagaagca | ggccaaaaaa | attagtgagc | 700 |
| aaccatccat | atttgacgaa | aacgatgccc | atgatctgta | tttccaaata | 750 |
| aaggaaatga | gtgaaaatga | aaaaattcac | gagaaggtgt | tgaaggccgc | 800 |
| tttattgaac | agaggagcag | aatctgttag | acgatcatta | aagttaaaag | 850 |
| agttggctcc | tcagataaac | cttctatata | aaaatggctc | tattggggag | 900 |
| gattactgga | agagatttga | aactgaagtt | aaattaattg | aattggaatt | 950 |
| taaagatact | ttacaagaag | ctgaaagatt | gcaaccgggc | tgggttcaat | 1000 |
| tgttcgttat | ggtttgtaaa | gaaatttgct | ttaatcaagc | tctctctaga | 1050 |
| cgttatcaat | caatcttgaa | acggaaagaa | gtgtgtatta | aagagtggga | 1100 |
| gctgaaaata | aataatgatg | gaagattagt | caattagtgc | ctactgtgtg | 1150 |
| caaagatatg | tattcgctcg | ttcagtgttt | ttttaaaaat | atgtatagaa | 1200 |
| tttgtcatta | tctgcgttaa | aaaatagtta | taagtatat | acaataacaa | 1250 |
| taaatgataa | agaaatatgc | agtgaaaaga | aaaaattatg | aagcttttcc | 1300 |
| tttcagtgtt | ttctaccctt | cttcttgctc | actacttgga | attcccagcc | 1350 |
| gtcgtcatca | ttgcctgata | gagctagcgc | ttcattccaa | cttagtggat | 1400 |
| catcaccttg | ttttcgcac | gcaacacgtc | ttttaataaa | ttcagtggca | 1450 |
| aatcttctac | catccataac | gtcactattg | gcataaattg | tttcttgaat | 1500 |
| caattcttta | gattctggcc | ccgtaggtaa | actcaataat | agttctaaga | 1550 |
| cattgttatt | ggttattcca | gaatttaatt | tcatctgtga | tttacaccat | 1600 |
| ttgataaatt | cttgccgggg | agaaacattg | ttcatgctag | caaaggtagt | 1650 |
| ggtagtagaa | gtctcgactc | tagaggatcc | ccgg | | 1684 |

<210> SEQ ID NO 10
<211> LENGTH: 1689
<212> TYPE: DNA
<213> ORGANISM: Saccharomyces cerevisiae

<400> SEQUENCE: 10

| | | | | | |
|---|---|---|---|---|---|
| gattacgcca | agcttgcatg | ccagcatgtc | accgtgcttt | agtcctagat | 50 |
| ccatcactgt | tcgatcagct | agttcagaaa | cagcatgaat | accttgaccg | 100 |
| ggcttctcac | aaacagtaaa | tgtgtcgaca | tcggcattgg | ggtccagatt | 150 |
| acccaccaac | ttttcaatga | ccgttccgaa | aaggtcgttt | tcttgacaag | 200 |
| aaaccctgtg | tgtaccgttt | tttgatctaa | atctgataag | catacttcac | 250 |
| ttaaatgtat | atcgatatca | gtagtatagg | gaaattttc | ttcagagtac | 300 |
| tgtcctatta | tttgccactc | ttcgttctgt | atgttacgag | ggcgttcctt | 350 |
| aaaatgggta | gacgcatctt | attacccgcc | aaaaacgtc | aaagtttta | 400 |
| ggaacacgtc | taaagttga | ataatatgt | gaaaaattg | atgaaatatt | 450 |
| aatgaaatgg | cttatttaaa | cgaattcaag | tacaggaaaa | aggtacgcac | 500 |
| aactacttga | gtttgccaat | atgtccgaat | ttaatgaaac | aaaattctcc | 550 |
| aacaacggga | cgttttttga | aacggaagag | ccaattgtgg | agacgaaatc | 600 |
| aatctccgtt | tataccccac | tcatatatgt | ctttattctg | gtggtgtccc | 650 |
| ttgtgatgtt | tgcttcaagc | tacagaaaga | agcaggccaa | aaaaattagt | 700 |
| gagcaaccat | ccatatttga | cgaaaacgat | gcccatgatc | tgtatttcca | 750 |
| aataaaggaa | atgagtgaaa | atgaaaaaat | tcacgagaag | gtgttgaagg | 800 |
| ccgctttatt | gaacagagga | gcagaatctg | ttagacgatc | attaaagtta | 850 |
| aaagagttgg | ctcctcagat | aaaccttcta | tataaaaaat | ggctctattg | 900 |
| gggaggatta | ctggaagaga | tttgaaactg | aagttaaatt | aattgaattg | 950 |
| gaatttaaag | atactttaca | agaagctgaa | agattgcaac | cgggctgggt | 1000 |
| tcaattgttc | gttatggttt | gtaaagaaat | ttgctttaat | caagctctct | 1050 |
| ctagacgtta | tcaatcaatc | ttgaaacgga | agaagtgtg | tattaaagag | 1100 |
| tgggagctga | aaataaataa | tgatggaaga | ttagtcaatt | agtgcctact | 1150 |
| gtgtgcaaag | atatgtattc | gctcgttcag | tgtttttta | aaaatatgta | 1200 |
| tagaatttgt | cattatctgc | gttaaaaaat | agttataaag | tatatacaat | 1250 |
| aacaataaat | gataaagaaa | tatgcagtga | aagaaaaaa | ttatgaagct | 1300 |
| tttcctttca | gtgttttcta | cccttcttct | tgctcactac | ttggaattcc | 1350 |
| cagccgtcgt | catcattgcc | tgatagagct | agcgcttcat | tccaacttag | 1400 |
| tggatcatca | ccttgttttt | cgcacgcaac | acgtctttta | ataaattcag | 1450 |
| tggcaaatct | tctaccatcc | ataacgtcac | tattggcata | aattgtttct | 1500 |
| tgaatcaatt | ctttagattc | tggccccgta | ggtaaactca | ataatagttc | 1550 |
| taagacattg | ttattggtta | ttccagaatt | taatttcatc | tgtgatttac | 1600 |
| accatttgat | aaattcttgc | cggggagaaa | cattgttcat | gctagcaaag | 1650 |
| gtagtggtag | tagaagtctc | gactctagag | gatccccgg | | 1689 |